United States Patent
Srivastava et al.

(10) Patent No.: US 7,269,586 B1
(45) Date of Patent: Sep. 11, 2007

(54) PATIENT RULE INDUCTION METHOD ON LARGE DISK RESIDENT DATA SETS AND PARALLELIZATION THEREOF

(75) Inventors: Anurag Srivastava, Foster City, CA (US); Vineet Singh, Cupertino, CA (US)

(73) Assignee: Hitachi America, Ltd., Tarrytown, NY (US)

( * ) Notice: Subject to any disclaimer, the term of this patent is extended or adjusted under 35 U.S.C. 154(b) by 0 days.

(21) Appl. No.: 09/470,444

(22) Filed: Dec. 22, 1999

(51) Int. Cl.
G06F 17/30 (2006.01)
G06F 7/00 (2006.01)
G06F 17/60 (2006.01)

(52) U.S. Cl. .................. 707/6; 707/5; 705/2; 705/3
(58) Field of Classification Search .................. 707/6, 707/5, 4; 705/2, 3
See application file for complete search history.

(56) References Cited

U.S. PATENT DOCUMENTS 5,787,274 A * 7/1998 Agrawal et al. ............ 707/102

(Continued)

FOREIGN PATENT DOCUMENTS

WO WO9406088 * 3/1994

(Continued)

OTHER PUBLICATIONS

Xindong Wu, "Induction by attribute Elimination", Knowledge and data Engineering, IEEE Transactions on vol. 11 issue: 5 Sep./Oct. 1999.*

Jorme et al. "Bump Hunting in High-dimensional data", Kluwer Academic Publishers, Hingham, MA, USA, p. 123-143, Year pf publication 1999.*

(Continued)

Primary Examiner—Frantz Coby
Assistant Examiner—Cindy Nguyen
(74) Attorney, Agent, or Firm—Dorsey & Whitney LLP

(57) ABSTRACT

The present invention relates to analysis of large, disk resident data sets using a Patient Rule Induction Method (PRIM) in a computer system wherein a relational data table is initially received. The relational data table includes continuous attributes, discrete attributes, a matter parameter and a cost attribute. The cost attribute represents cost output values based on continuous attribute values and discrete attribute values as inputs. A hyper-rectangle is then formed which encloses a multi-dimensional space defined by the continuous attribute values and the discrete attribute values. The continuous attribute values and the discrete attribute values are represented as points within the multi-dimensional space. A plurality of points along edges of the hyper-rectangle are then removed based on an average of the cost output value from the plurality of points until a count of the points enclosed within the hyper-rectangle equals the meta parameter. Discrete attribute values and continuous attribute values which were removed from the hyper-rectangle are next added along edges of the hyper-rectangle until a sum of the cost output value over the multi-dimensional space enclosed by the hyper-rectangle changes. In a further embodiment a parallel architecture computer system calculates the cost attribute average values over the plurality of points enclosed by the hyper-rectangle in parallel. The invention analyzes large disk resident data sets without having to load the data set into main memory and can be practiced on a parallel computer architecture or a symmetric multi-processor architecture to improve performance.

19 Claims, 20 Drawing Sheets

U.S. PATENT DOCUMENTS

| | | | | |
|---|---|---|---|---|
| 5,813,019 A | | 9/1998 | Van de Vanter | 707/512 |
| 5,960,435 A | * | 9/1999 | Rathmann et al. | 707/101 |
| 5,991,728 A | * | 11/1999 | DeBusk et al. | 705/2 |
| 6,229,918 B1 | * | 5/2001 | Toyama | 382/173 |
| 6,307,965 B1 | * | 10/2001 | Aggarwal et al. | 382/225 |
| 6,563,952 B1 | * | 5/2003 | Srivastava et al. | 382/225 |

FOREIGN PATENT DOCUMENTS

| | | | |
|---|---|---|---|
| WO | WO9726609 | * | 7/1997 |

OTHER PUBLICATIONS

Friedman et al., "Bump Hunting In High-Dimesional Data," Dept. of Statistics and Stanford Linear Accelerator Center, Stanford University, Stanford, CA 94305, Oct. 28, 1998, pp. 1-31.

Mehta et al., "SLIQ: A Fast Scalable Classifier for Data Mining," IBM Almaden Research Center, 650 Harry Road, San Jose, CA 95120.

Srivastava et al., "An Efficient, Scalable, Parallel Classifier for Data Mining," Dept. of Computer Science, University of Minnesota, Dept. of Computer Science, 4-192 EE/CS Bldg., 200 Union St. SE, Minneopolis, MN 55455.

* cited by examiner

HYPER BOX DEFINED AS 50 < AGE < 70 AND 2 < = STAY LENGTH < = 4

DOCTOR ID HISTOGRAM

| DOCTOR ID | | | | |
|---|---|---|---|---|
| | A | B | C | D |
| EXPECTED COST | 150 | 200 | 900 | 1000 |

$$\text{EXPECTED COST} = \frac{\sum \text{COST}}{\text{\# OF INSTANCES OF THE DISCRETE ATTRIBUTE VALUE}}$$

RELATIONAL TABLE OF DATA

| INDEX | DOCTOR ID | AGE | LENGTH OF STORAGE | COST |
|---|---|---|---|---|
| | A | 20 | 1 | 100 |
| 2 | A | 40 | 2 | 300 |
| | B | 16 | 1 | 100 |
| 4 | B | 60 | 3 | 1000 |
| 5 | C | 70 | 2 | 800 |
| • | • | • | • | • |
| • | • | • | • | • |
| • | • | • | • | • |
| 100 | D | 50 | 4 | 1500 |

FIG. 2
PRIOR ART

Original sorted list

Processor 1    Processor 2    Processor 3    Processor 4

PATIENT RULE INDUCTION METHOD ON LARGE DISK RESIDENT DATA SETS AND PARALLELIZATION THEREOF

The present invention relates generally to data analysis involving the prediction of high values of some output variable based on a set of input variables. In particular, the invention relates to analysis of large, disk resident data sets using the Patient Rule Induction Method (PRIM).

BACKGROUND OF THE INVENTION

A generic problem in data analysis involves the prediction of high values of some output variable based on a set of input variables. For example, a hospital might want to determine from collected patient data what combinations of patient age and length of stay are associated with high cost hospital stays. Adding to the complexity of this data analysis problem is the fact that the variables of interest can be of different types, including:

continuous/numerical (ordered data, such as age, cost, length of stay);

categorical (non-ordered data, such as doctor); and discrete (ordered, non-continuous data, such as procedure risk).

There are many prior art strategies for solving similar data analysis problems to the one described above, including the SLIQ classification algorithm (M. Mehta, R. Agrawal and J. Rissanen, *SLIQ: A Fast Scalable Classifier for Data Mining*, Proc. of the Fifth Int'l Conference on Extending Database Technology, Avignon, France, March 1996.), SPEC (*An Efficient, Scalable, Parallel Classifierfor Data Mining* (1996) Anurag Srivastava, Vineet Singh, Eui-Hong (Sam) Han and Vipin Kumar, Technical Report 96-040, Department of Computer Science, University of Minnesota, Minneapolis, 1996.), and the Patient Rule Induction Method (PRIM) (Friedman, J. H. and Fisher, N. I. *Bump Hunting in High-Dimensional Data* (October 1997) (to appear in Statistics and Computation). In each of these strategies, the data to be analyzed is stored initially in a database of any type and the data analysis system copies the stored data onto disk using specific data structures that facilitate analysis of the data.

The SLIQ classification algorithm finds local groups of the input data that have a high output value. It works better with categorical data than with continuous data. That is, the SLIQ algorithm is more likely to find contiguous groups of multi-dimensional input data with high output values for categorical rather than continuous data. Because of this, the SLIQ algorithm is typically paired with linear regression analysis when continual data needs to be analyzed.

The PRIM algorithm, on which the present invention is based, specifically addresses the issue of determining regions in a multidimensional space of a set of input variables that correspond to high average for an output variable. Moreover, the regions generated by PRIM are easily interpretable as they are rectangles for two input variables or (more generally) hyper-rectangles for more than two input variables. (Note, for the remainder of this application, the terms "hyper-rectangles" and "boxes" are used interchangeably.) A comparison of the results given by the SLIQ and PRIM algorithms for the same input is now described with reference to FIG. 1.

Referring to FIG. 1, there is shown a plot where the input variables are Length Of Stay and Age for hospital patients and the output variable is Charge for the patient's stay, where points that are filled-in are high value points and points that are not filled in are low value points. Given the goal of finding those regions of the Length of Stay/Age space with highest Charge, the PRIM algorithm would return the single hyper-rectangle 102, whereas the SLIQ algorithm would return the smaller, disjoint regions 104*a*, 104*b*. The PRIM hyper-rectangle region 102 description (e.g., 50<Age<70 and 2<=Stay Length<=4) can be used for prediction applications where the input variables are known and the output variable is unknown. In particular, for a hospital application, the high charge (or high cost) patients may be used to reduce costs internally or to negotiate more profitable contracts with payors (or insurance companies) externally. This application is facilitated by the simpler output of PRIM as compared to that from the SLIQ algorithm. As the present invention is based on PRIM, this method is now described in greater detail.

The idea behind PRIM is to enclose all input data points within a single hyper-rectangle and then successively peel away contiguous, small strips of the hyper-rectangle enclosing low value points until a user-defined percentage of the total points remain inside the hyper-rectangle. These points are presumed to be predominantly high value points. PRIM can be applied to a small data set that can be copied in its entirety into main memory (i.e., RAM accessible to executing programs), but is not able to handle larger data sets. PRIM includes the following steps for continuous data:

1) copy the entire data set into main memory;

2) define a peeling fraction ($\alpha$) which is the width of the contiguous, small strips of the hyper-rectangle. Each strip is formed by grabbing a given percentage of the initial points which is preferable between 1% and 5% of the points along the perimeter of the hyper-rectangle.

3) form the strips along edges of the hyper-rectangle by taking $\alpha$% of the points along the perimeter of the hyper-rectangle.

4) calculate an average value of the cost attribute for each strip of the hyper-rectangle. For each attribute, sort the data and find the average value of the cost attribute for $\alpha$% of the top points and $\alpha$% of the bottom points. This is repeated for each attribute.

5) throw away the strip with the lowest average cost value and return to step 3)—repeat until the number of points remaining enclosed by the hyper-rectangle equals a user-defined percentage of the initial points (the remaining points will be the user-defined percentage of points with the highest average output value).

The steps for discrete data are similar to the previously described steps, except, instead of multi-dimensional strips, histograms are used. For example, if one of the input variables were Doctor ID, each strip would correspond to a histogram bin for a given Doctor ID. The way PRIM is implemented for small data sets is now described with reference to FIG. 2.

Referring to FIG. 2, there is shown an illustration of a data structure used by the prior art PRIM implementation for discrete attributes and a relational table of data. The relation table of data contains both continuous attributes and discrete attributes. To process the discrete attribute Doctor ID, a histogram is generated containing all distinct Doctor Ids and an expected cost. The expected cost is calculated by summing the cost for each record with each Doctor ID and dividing the sum by a count of each record with the Doctor ID. As depicted in FIG. 2, the Doctor IDs A, B, C and D are shown along with the expected cost. The Doctor ID A has the lowest expected cost ($100.00) and is therefore chosen as the peeling discrete attribute.

Consequently, the PRIM calculation for discrete attributes is exactly as described above for continuous. However for discrete attributes, step 4) would include forming a histogram for each discrete attribute containing the distinct discrete attribute values and expected cost. Step 5) would include comparing the continuous attribute with the lowest average value to the discrete attribute with the lowest average value to determine the peeling attribute to be removed.

The PRIM implementation described above must sort the relation table of data for each attribute one at a time for each peeling step. In addition, the relational table of data must be queried to determine the expected cost for each discrete attribute for each peeling step. These tasks require that the relational table of data be stored in main memory. Unfortunately, memory limitations of conventional systems prevent large disk resident data sets from being entirely sorted in main memory. Therefore, there is a need for an implementation of PRIM that is applicable to large, disk-resident data sets. There is also a need for an implementation of PRIM that can be parallelized for execution on parallel processors.

SUMMARY

The invention overcomes the identified problems by providing a method for analyzing large disk resident data sets. In a computer system having a large disk-resident data set, a method of analyzing the disk-resident data set using the Patient Rule Induction Method (PRIM) is disclosed wherein a relational data table is initially received. The relational data table includes continuous attributes, discrete attributes, a meta parameter and a cost attribute. The cost attribute represents cost output values based on continuous attribute values and discrete attribute values as inputs. A hyper-rectangle is then formed which encloses a multi-dimensional space defined by the continuous attribute values and the discrete attribute values. The continuous attribute values and the discrete attribute values are represented as points within the multi-dimensional space. Once the hyper-rectangle is formed, PRIM is completed with a peeling phase and a pasting phase. A plurality of points along edges of the hyper-rectangle are then removed (peeled) based on an average of the cost output value from the plurality of points until a count of the points enclosed within the hyper-rectangle equals the meta parameter. Discrete attribute values and continuous attribute values which were removed from the hyper-rectangle are next added (pasted) along edges of the hyper-rectangle until a sum of the cost output value over the multi-dimensional space enclosed by the hyper-rectangle changes. In a further embodiment of the invention utilizing a parallel architecture computer system having a plurality of processors, calculations of the cost attribute average values over the plurality of points enclosed by the hyper-rectangle are performed in parallel across the plurality of processors using reduction and a one to all broadcast.

The invention provides many advantages over known techniques. The present invention includes the ability to analyze large disk resident data sets without having to load the data set into main memory. In addition, the invention can be practiced on a parallel computer architecture or a symmetric multi-processor architecture to improve performance. Moreover, the memory requirements of the invention are only limited by the size of the cost attribute sought to be maximize or minimized.

BRIEF DESCRIPTION OF THE DRAWINGS

Additional advantages and features of the invention will become readily apparent upon reading the following detailed description and appended claims when taken in conjunction with reference to the drawings, in which:

FIG. 2 depicts data structures used by the Patient Rule Induction Method for analysis of small data sets;

DETAILED DESCRIPTION

The present invention relates generally to data analysis involving the prediction of high values of some output variable based on a set of input variables. In particular, the invention relates to analysis of large, disk resident data sets using the Patient Rule Induction Method (PRIM). The PRIM method for large disk resident data sets includes two phases for generating a hyper-rectangle. These phases are the Peeling phase and the Pasting phase. We assume that the data is input as a relational data table. The relational data table contains $A_c$ continuous attributes, $A_d$ discrete attributes and a cost attribute or output value based on the $A_c$ continuous attributes and $A_d$ discrete attributes as input. In order to simplify this discussion, the term cost attribute is generally used to refer to output values based on continuous attribute values and discrete attribute values as inputs. In other words, a cost output value is an output based on a continuous attribute value and a discrete attribute value as inputs. $\beta_0$ is meta parameter given by the user. It represents the minimum number of points present in the hyper-rectangle.

Figure 1:
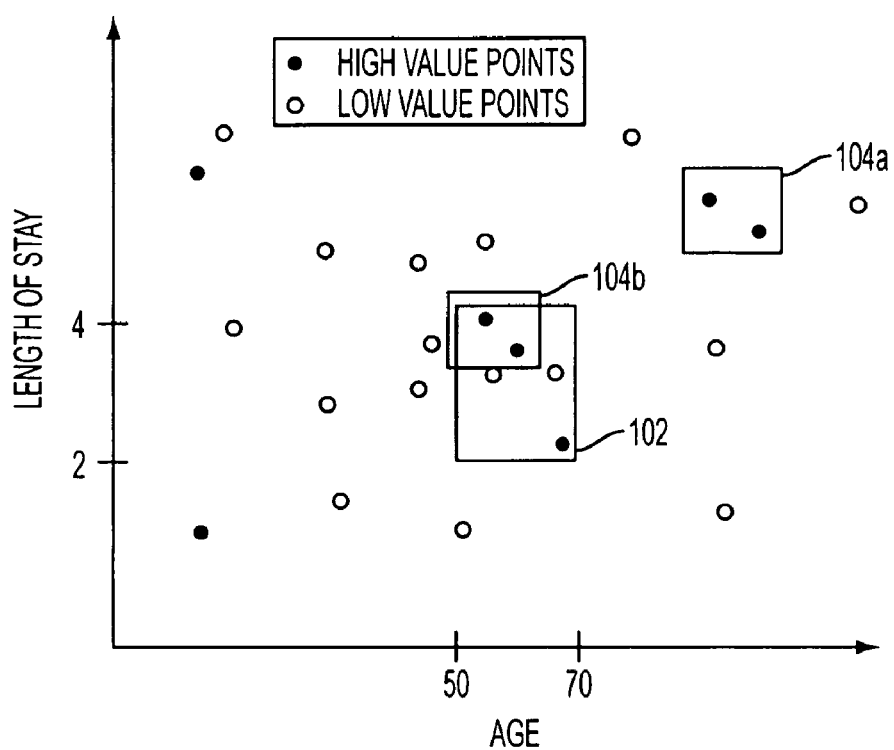
FIG. 1 is a plot depicting the hyper-rectangles determined using the methods of the present invention as compared to the prior art SLIQ invention.
Figure 3:
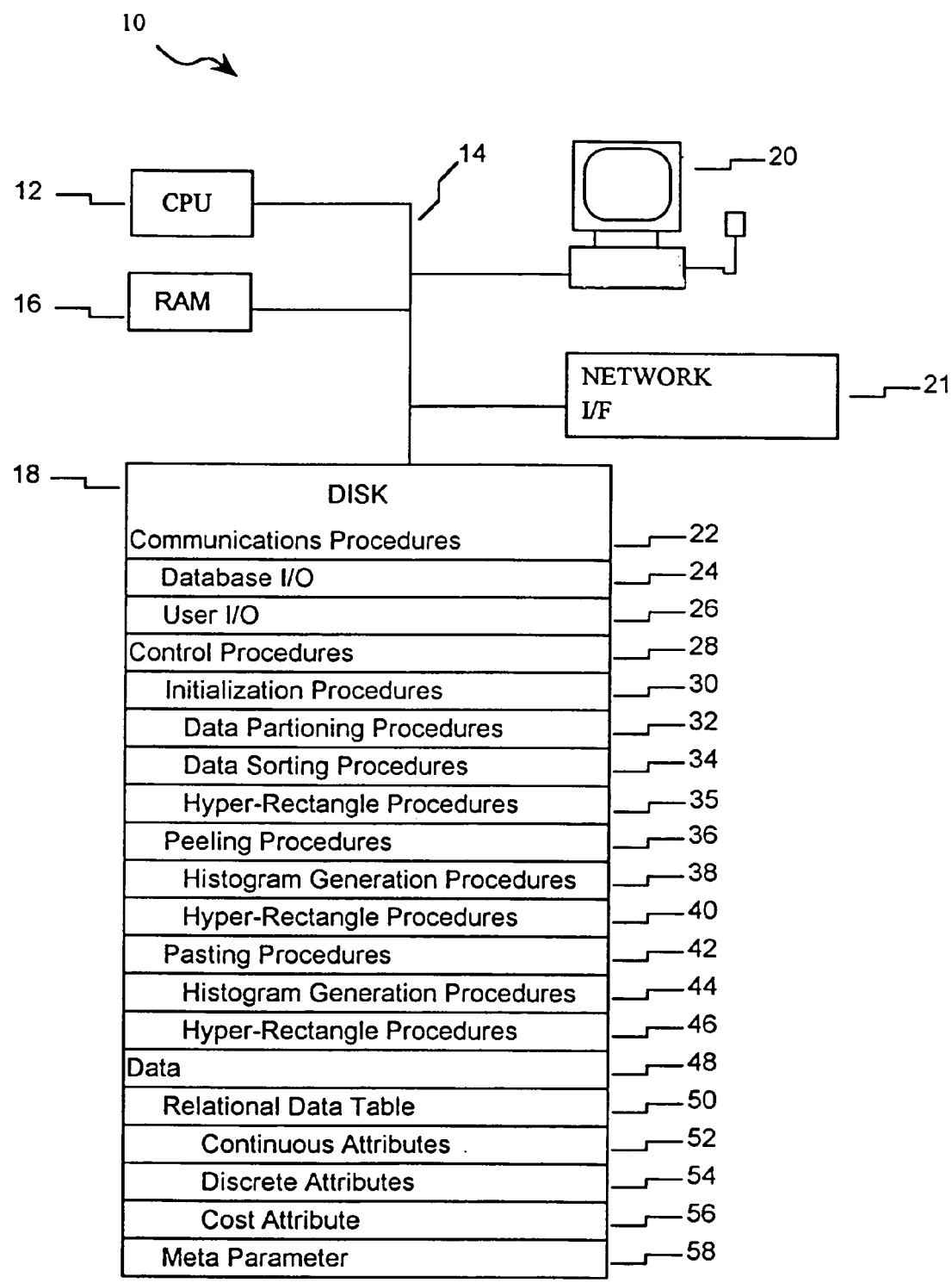
FIG. 3 depicts a computer system according to an embodiment of the invention.
Figure 4:
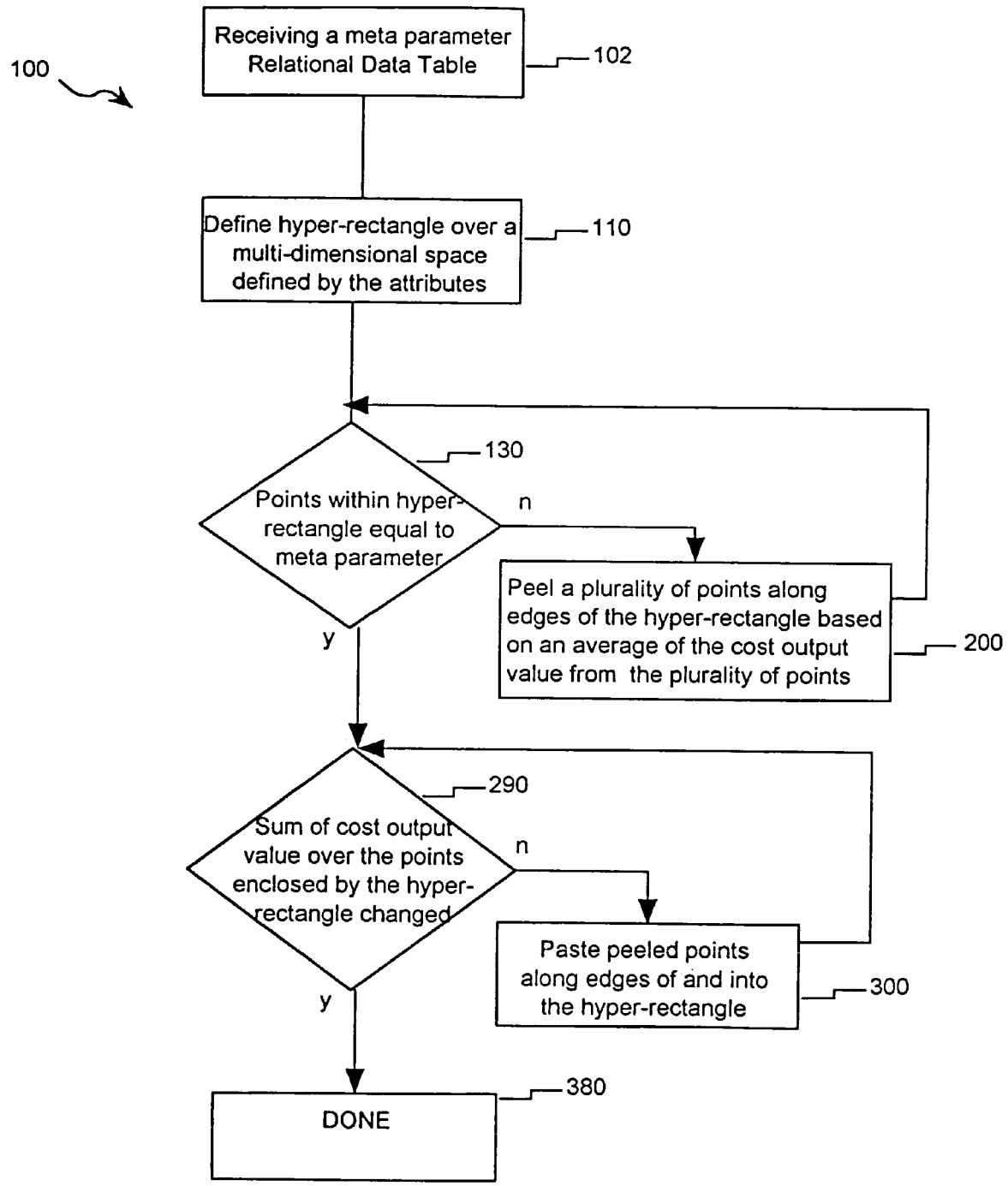
FIG. 4 is a flow chart depicting operation of the invention according to an embodiment of the invention.

An exemplary embodiment of the invention is described with reference to FIGS. 3 and 4. FIG. 3 depicts a computer system 10 according to an embodiment of the invention. The computer system includes a processor (CPU) 12 coupled to a bus 14. A random access memory 16 and a hard disk memory 18 are also coupled to the bus 14 and are accessible by the processor. The hard disk 18 is configured to store programs and data necessary for the invention, as described below. An optional user interface 20 is provided for input of raw data. In one embodiment, the input/output devices include a keyboard, mouse, and monitor. An optional network interface 21 is also provided. It should be appreciated that raw data may be entered in various different ways, for example via the user interface 20 or the network interface 21.

The hard disk 18 is configured to store the program and data in the computer system 10. The memory, including the RAM and the hard disk, is divided into three primary components: communications procedures 22, control procedures 28, and data 42. The communications procedures include routines 24 and 26 for identifying large disk resident data sets. The control procedures include routines 30-46 that perform data analysis functions according to the invention. The data portion creates indexes to an $A_c$ continuous attribute lists and a discrete attribute list of the relational data table 54, and stores a cost list, and a meta parameter 50 in main memory (RAM) 16. These routines are described in greater detail below.

Operation of the invention is described with reference to the FIG. 4 flowchart. At step 102, a meta parameter and a relational data table are received. As described above, the relational data table includes $A_c$ continuous attributes, discrete attributes and a cost attribute. The cost attribute represents cost output values based on continuous attributes values and discrete attribute values as inputs. The attributes are originally rows or tuples that form the relational data table which also contains an index to identify the tuple when the attributes are separated. At step 110, a hyper-rectangle is defined by enclosing a multi-dimensional space defined by the continuous attribute values and the discrete attribute values. To form the multi-dimensional space, the continuous attribute values and the discrete attribute values are represented as points within the multi-dimensional space. At steps 130 and 200, a plurality of points along edges of the hyper-rectangle are removed (peeled) based on an average of the cost output value from the plurality of points. The points are repeatedly removed until a count of the points enclosed within the hyper-rectangle equals the meta parameter. Finally at steps 290 and 300, removed discrete attribute value points and the continuous attribute value points are added (pasted) along the edges of the hyper-rectangle until a sum of the cost output values over the multi-dimensional space enclosed by the hyper-rectangle changes.

Figure 5:
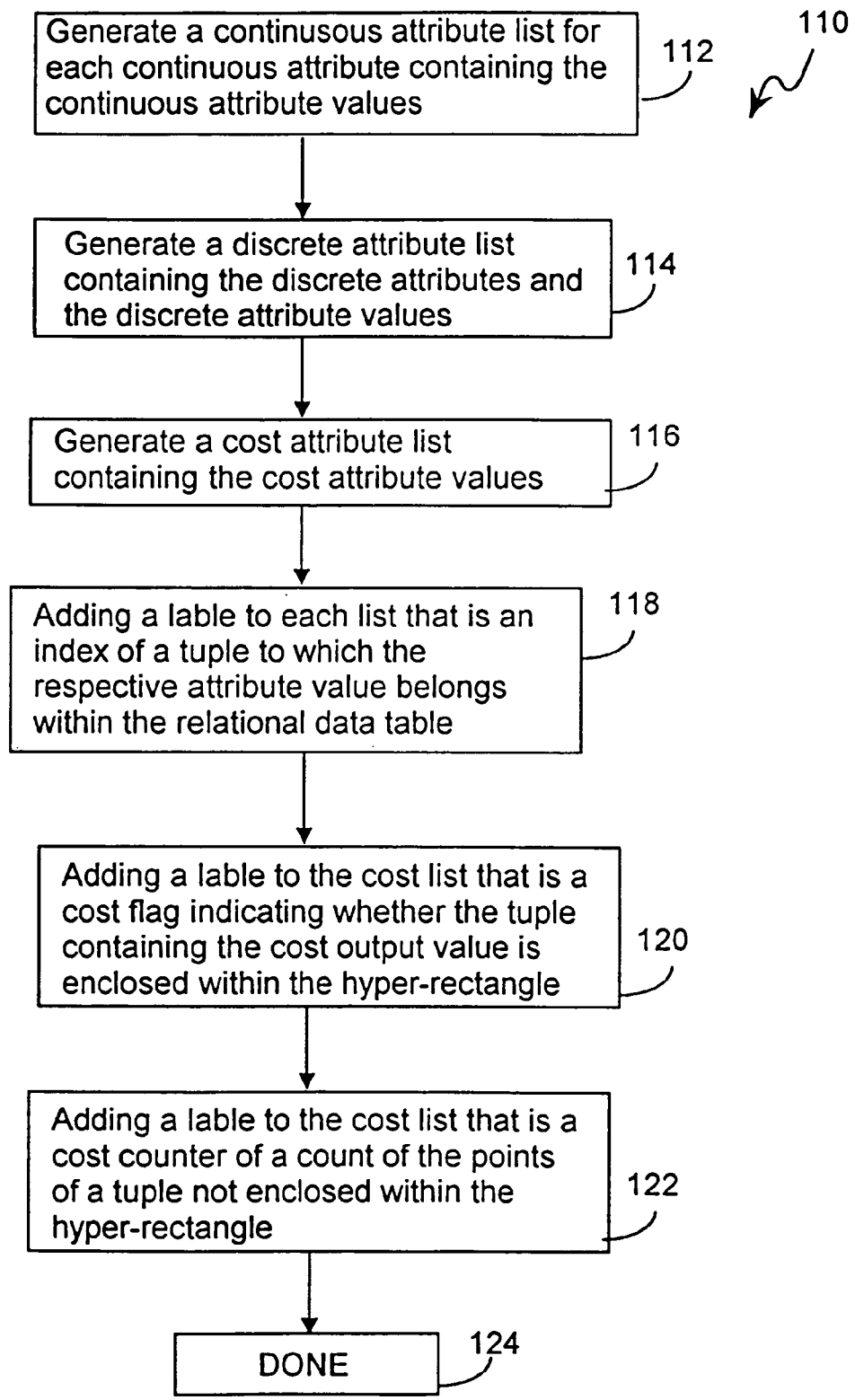
FIG. 5 depicts additional method steps for defining the hyper-rectangle according to a further embodiment of the invention.

FIG. 5 depicts additional methods steps for defining the hyper-rectangle of step 110 according to a further embodiment of the invention. FIG. 5 depicts vertical partitioning of the relational data table that enables analysis of the large disk resident data set without having to load the large disk resident data set into main memory 16 as required by conventional systems. The data is separated into $A_c+2$ lists. At step 112, a list is generated for each continuous attribute to form $A_c$ continuous attribute lists containing the continuous attribute values. At step 114, a discrete attribute list containing the $A_d$ discrete attributes and the discrete attribute values is generated. At step 116, a cost attribute list is generated containing the cost output values and is stored in main memory. At step 118, a label is added to each of the $A_c$ continuous attribute lists, the discrete attribute list and the cost attribute list. The label is an index of the tuple to which the respective attribute value belongs within the relational data table. The index allows the continuous attribute values and discrete attribute values to reference their respective tuple and cost output value.

At step 120, a label is added to the cost list. The label is a cost flag that indicates whether the tuple containing the cost output value is enclosed within the hyper-rectangle. The cost flag is initially set to one indicating the tuple is enclosed within the hyper-rectangle, since all points are initially enclosed within the hyper-rectangle. Finally at step 122, a further label is added to the cost list. The label is a cost counter of the number of points of the tuple that are not enclosed within the hyper-rectangle. The cost counter is initially set to one indicating since all points are initially enclosed with the hyper-rectangle. The cost counter is used in the pasting procedures 42.

Figure 6:
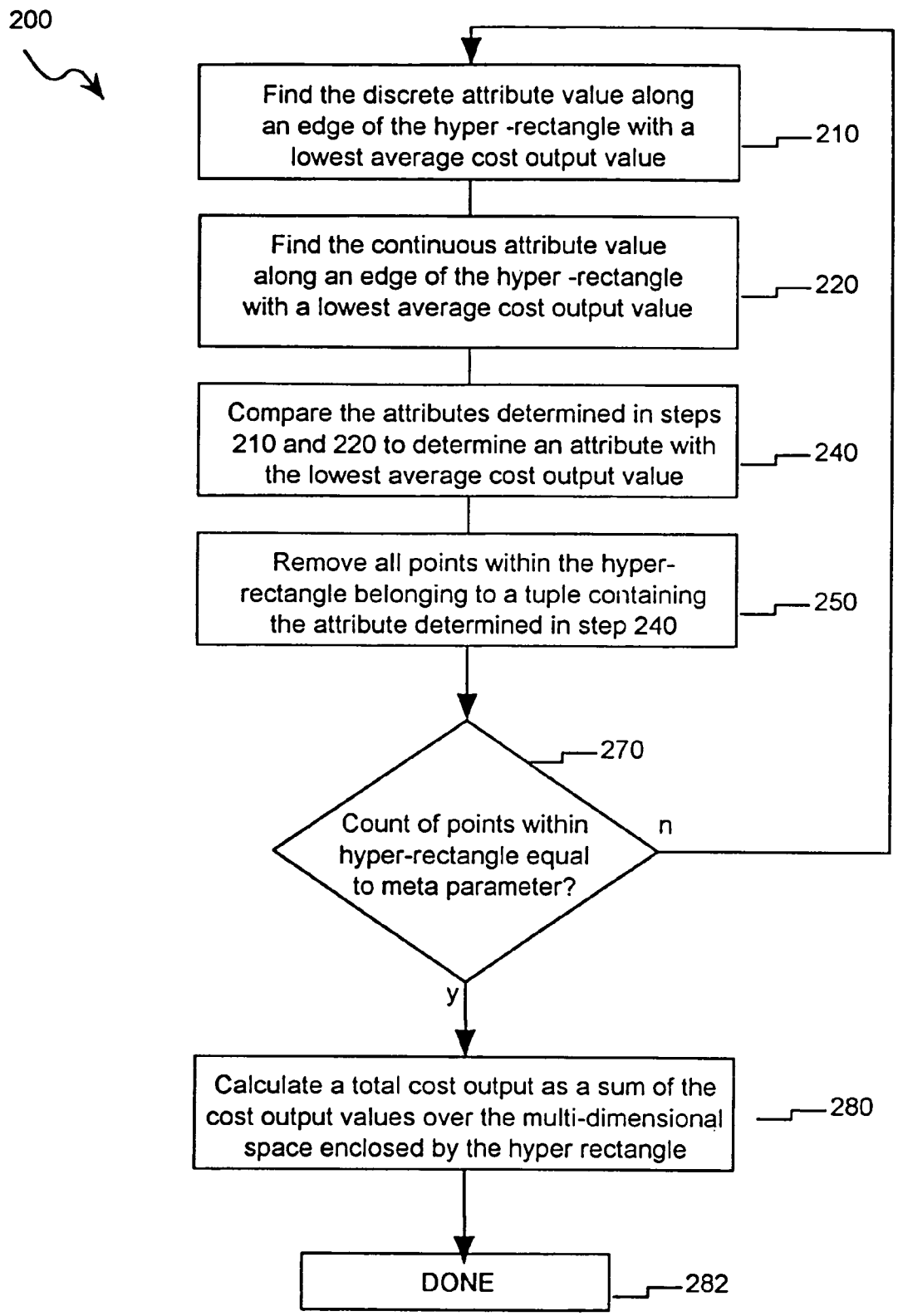
FIG. 6 depicts additional method steps for peeling procedures according to a further embodiment of the invention.

FIG. 6 depicts additional methods steps for the peeling procedures 36 of step 200 according to a further embodiment of the invention. At step 210, a discrete attribute value enclosed within the plurality of points along an edge of the hyper-rectangle with a lowest average cost output value is found. At step 220, the continuous attribute value enclosed within the plurality of points along an edge of the hyper-rectangle with a lowest average cost output value is found. At step 240, the lowest average cost output value determined in step 210 is compared with the lowest average cost output value determined in step 220 to determine an attribute with the lowest average cost output value. At step 250, all continuous attribute value points and all discrete attribute value points of the tuples containing the attribute determined in step 240 are removed (peeled) from the hyper-rectangle. At step 270, steps 210 to 250 are repeated until the count of the points within the hyper-rectangle equals $\beta_0$.

Finally at step 280, a total cost output is calculated. The total cost output is a sum of the cost output values over the multi-dimensional space enclosed by the hyper-rectangle. Although the peeling procedure described above is maximizing the points enclosed by the hyper-rectangle, the points enclosed by the hyper-rectangle could be minimized as well. In addition, the discrete attribute value of step 200 is, for example, determined using a plurality of discrete histogram for each discrete attribute. Each histogram contains the respective distinct discrete attribute values and an average of the cost output value for each tuple containing the discrete attribute value. The average cost output value is calculated by using the index of the discrete attribute value and totaling each cost output value in the cost list with a matching index and the cost flag equal to zero. The total is then divided by a count of the cost output values in the total to form the average cost output value for the respective discrete attribute value. The discrete attribute value with the lowest average cost output value is then easily chosen by examining each discrete histogram.

Figure 7:
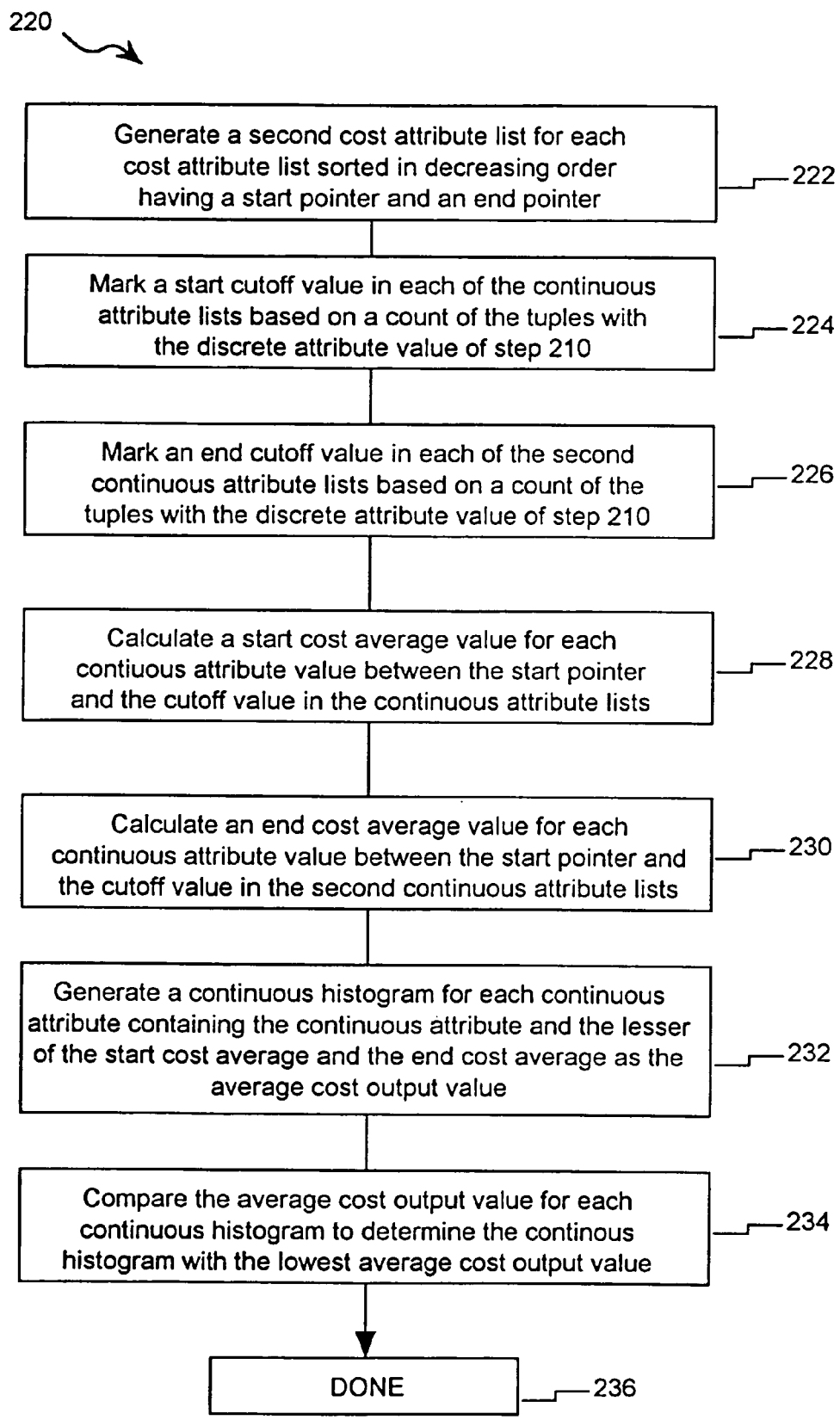
FIG. 7 depicts additional method steps for optimizing calculation of the lowest average cost output value according to a further embodiment of the invention.

FIG. 7 depicts additional methods steps for optimizing calculation of the lowest average cost output value of step 220 according to a further embodiment of the invention. Initially, each continuous attribute list is sorted in increasing order with a start pointer to a first row in each continuous attribute list. At step 222, a second continuous attribute list is generated for each of the $A_c$ continuous attribute lists. The second continuous attribute lists are sorted in decreasing order with an end pointer to a first row in each second continuous attribute list. At step 224, a start cutoff value is marked in each of the $A_c$ continuous attribute lists based on a count of the tuples containing the discrete attribute value determined in step 210 and enclosed within the hyper-rectangle. At step 226, an end cutoff value is marked in each of the second continuous attribute lists based on the count of the tuples containing the discrete attribute value determined in step 210 and enclosed within the hyper-rectangle.

At step 228, a start cost average value is determined for each continuous output value between the start pointer and the cutoff value for each of the $A_c$ cost attribute lists. At step 230, an end cost average value is determined for each continuous output value between the cutoff value and the end pointer for each of the second cost attribute lists. At step 232, $A_c$ continuous histograms, each containing the continuous attribute and the average cost output value, are generated. The average cost output value is a lesser of the start cost average value and the end cost average value. Finally at step 234, the average cost output value for each continuous histogram is compared to determine the continuous attribute value with the lowest average cost output value.

Figure 8:
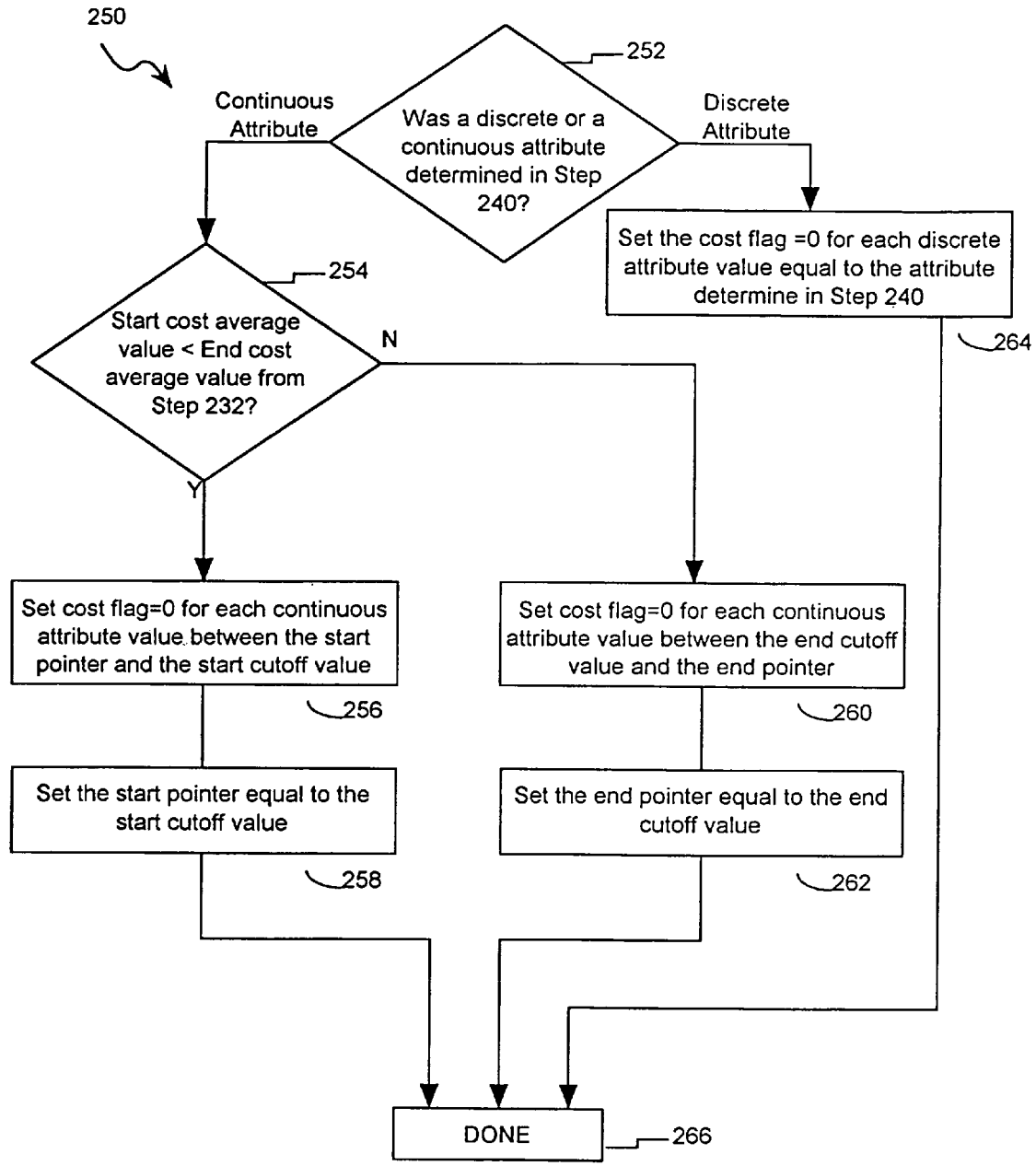
FIG. 8 depicts additional method steps for the peeling procedures according to a further embodiment of the invention.

FIG. 8 depicts additional methods steps for the peeling procedures 36 of step 250 according to a further embodiment of the invention. In order to optimize this process, the discrete attribute list is sorted based on an assigned code thereby grouping the discrete attribute values according to their discrete attribute. At step 252, when the attribute determined in step 240 is a continuous attribute and the start cost average value is less than the end cost average value (step 254), the cost flag is set to zero for each continuous attribute value between the start pointer and the start cutoff value at step 256. The index of the continuous attribute value is used to reference and modify the cost flag. At step 258, the start pointer is set equal to the start cutoff value. At step 254, when the end cost average value is less than the start cost average value, the cost flag is set to zero for each continuous attribute value between the end cutoff value and the end pointer at step 260. The index of the continuous attribute value is used to reference and modify the cost flag. At step 258, the end pointer is set equal to the end cutoff value. At step 252, when the attribute determined in step 240 is a discrete attribute, the cost flag is set to zero for each discrete attribute value equal to the attribute determined in step 240. The index of the discrete attribute value is used to reference and modify the cost flag.

Figure 9:
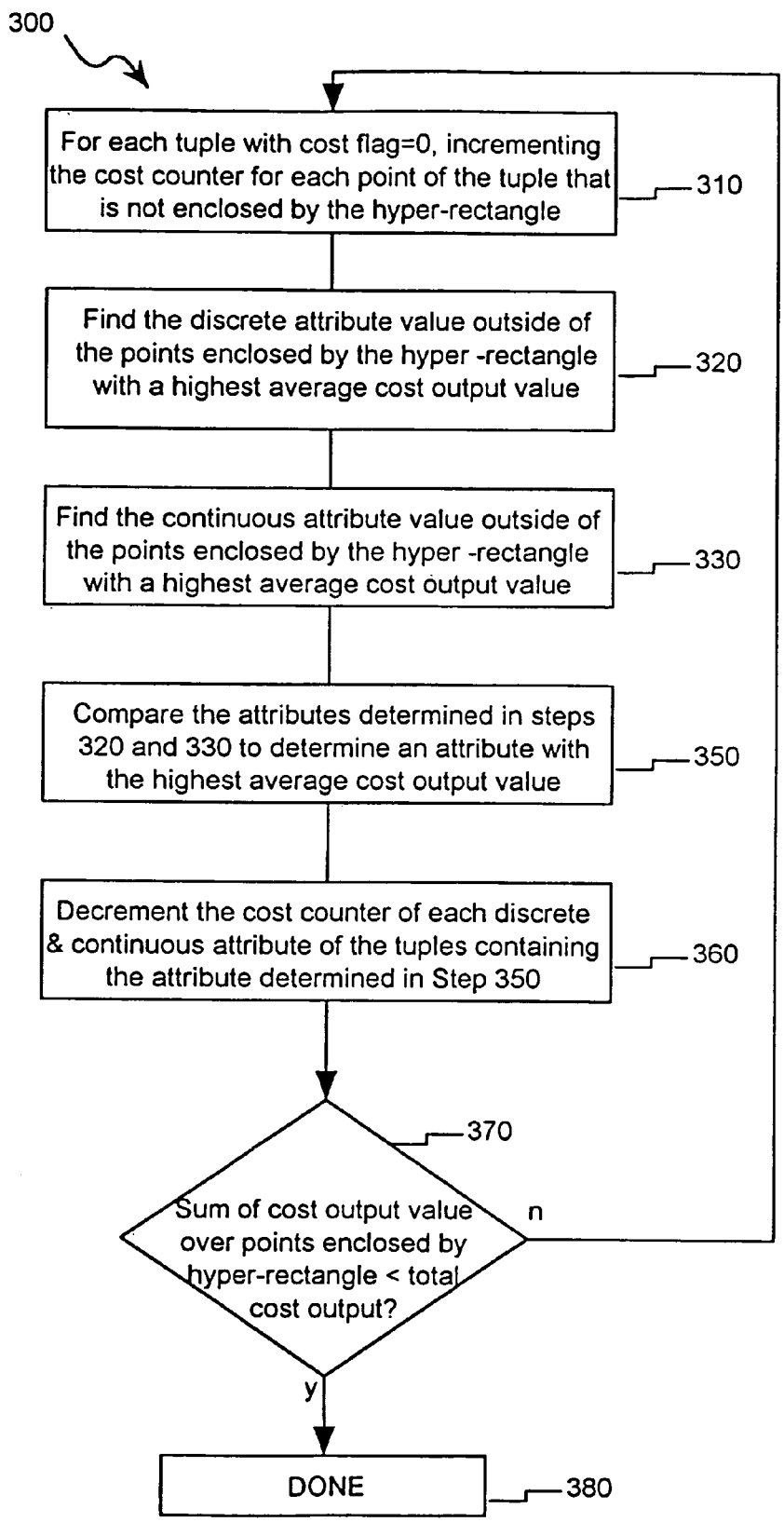
FIG. 9 depicts additional method steps for performing the pasting procedures according to a further embodiment of the invention.

FIG. 9 depicts additional methods steps for performing the pasting procedures 42 of step 300 according to a further embodiment of the invention. At step 310, for each tuple with the cost flag set to zero, the cost counter is incremented for each point belonging to the tuple that is not enclosed with the hyper-rectangle. The cost counter is used to determine whether a point is inside or outside the hyper-rectangle. At step 320, the discrete attribute value outside of the points enclosed by the hyper-rectangle with a highest average cost output value is determined. At step 330, the continuous attribute value outside of the points enclosed by the hyper-rectangle with a highest average cost output value is determined. At step 350, the highest average cost output value determined in step 320 is compared with the highest average cost output value determined in step 330 to find an attribute with the highest average cost output value. Finally at step 360, the cost counter for all continuous attribute value points and all discrete attribute value points belonging to the tuples containing the attribute determined in step 350 are decremented. Attributes with the cost counter equal to zero are enclosed within the hyper-rectangle, otherwise the attribute is outside the hyper-rectangle. In other words, incrementing of the cost counter removes attributes from the hyper-rectangle, while decrementing of the cost counter to equal zero adds attributes to the hyper-rectangle. At step 370, steps 310 to 360 are repeated until a sum of the cost output values over the plurality of points enclosed by the hyper-rectangle is less than the total cost output. This pasting procedure ensures a more through representation of high value points. As describe above, the highest average cost output value of step 320 is calculated using a plurality of discrete histograms.

Figure 10:
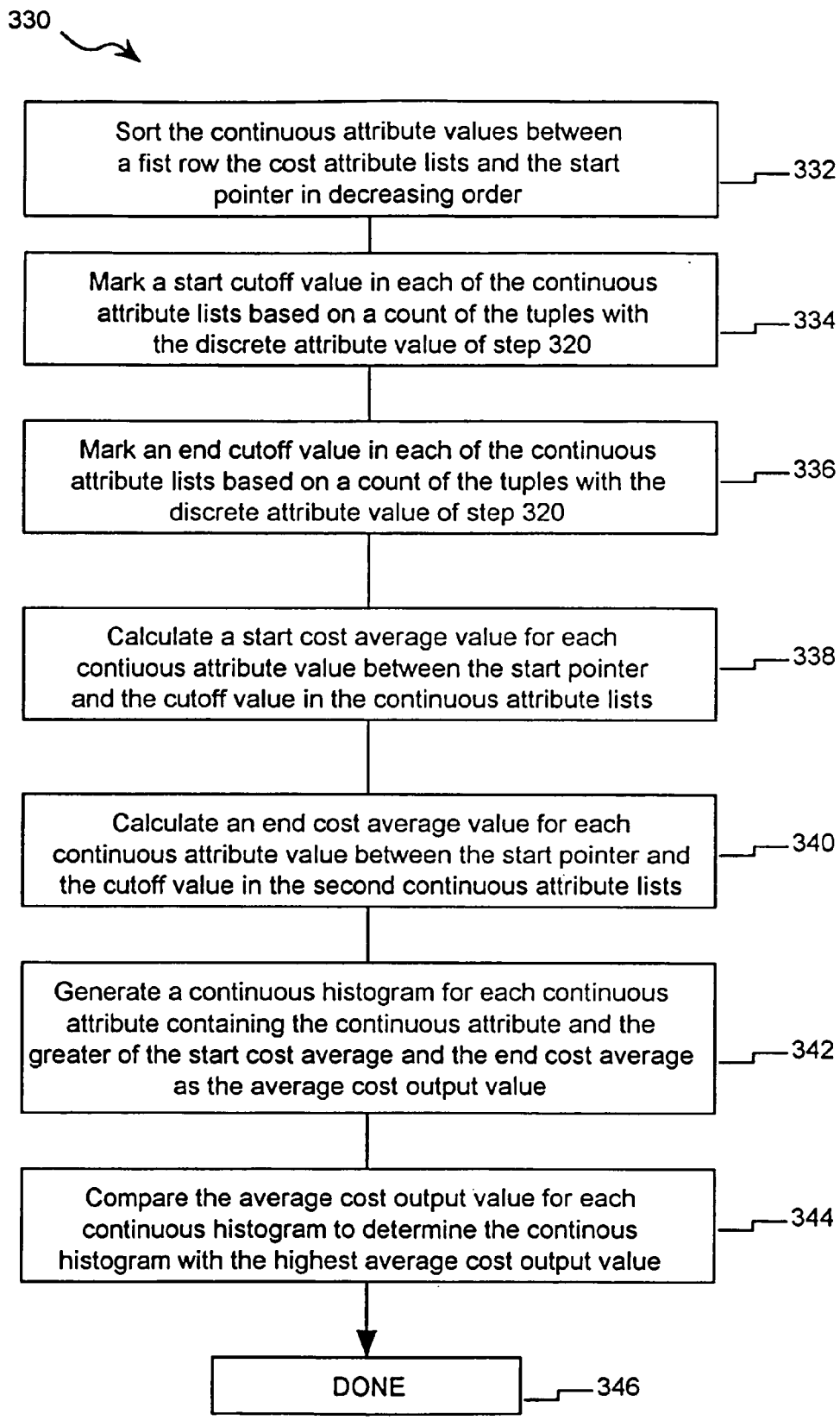
FIG. 10 depicts additional method steps for optimizing calculation of the highest average cost output value according to a further embodiment of the invention.

FIG. 10 depicts additional methods steps for optimizing calculation of the highest average cost output value of step 330 according to a further embodiment of the invention. At step 332, a the continuous attribute values between a first row of the $A_c$ cost attribute lists and the start pointer are sorted in decreasing order. At step 334, a start cutoff value is marked in each of the $A_c$ continuous attribute lists based on a count of the tuples containing the discrete attribute value determined in step 320 and enclosed within the hyper-rectangle. At step 336, an end cutoff value is marked in each of the second continuous attribute lists based on the count of the tuples containing the discrete attribute value determined in step 320 and enclosed within the hyper-rectangle.

At step 338, a start cost average value is determined for each continuous output value between the start pointer and the cutoff value for each of the $A_c$ cost attribute lists. At step 340, an end cost average value is determined for each continuous output value between the cutoff value and the end pointer for each of the second cost attribute lists. At step 342, $A_c$ continuous histograms, each containing the continuous attribute and the average cost output value, are generated. The average cost output value is a greater of the start cost average value and the end cost average value. Finally at step 344, the average cost output value for each continuous histogram is compared to determine the continuous attribute value with the highest average cost output value.

Figure 11:
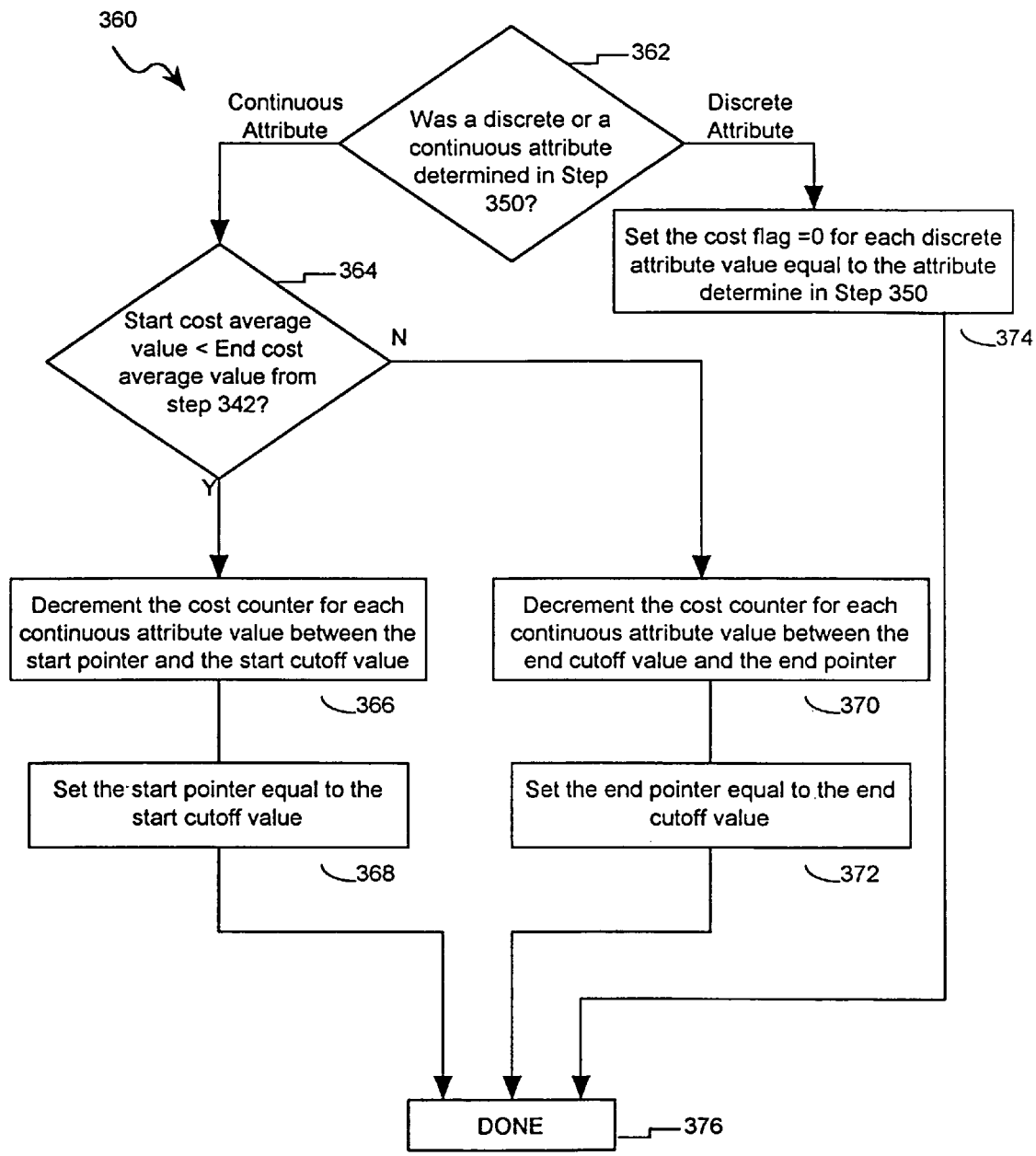
FIG. 11 depicts additional method steps for the pasting procedures according to a further embodiment of the invention.

FIG. 11 depicts additional methods steps for the pasting procedures 42 of step 360 according to a further embodiment of the invention. In order to optimize this process, the discrete attribute list is sorted based on an assigned code thereby grouping the discrete attribute values according to their discrete attribute. At step 362, when the attribute determined in step 350 is a continuous attribute and the start cost average value is less than the end cost average value (step 364), decrement the cost counter for each continuous attribute value between the start pointer and the start cutoff value at step 366. The index of the continuous attribute value is used to reference and modify the cost counter. At step 368, the start pointer is set equal to the start cutoff value. At step 374, when the end cost average value is less than the start cost average value, decrement the cost counter for each continuous attribute value between the end cutoff value and the end pointer at step 370. The index of the continuous attribute value is used to reference and modify the cost counter. At step 372, the end pointer is set equal to the end cutoff value. At step 362, when the attribute determined in step 350 is a discrete attribute, decrement the cost counter for each discrete attribute value equal to the attribute determined in step 350. The index of the discrete attribute value is used to reference and modify the cost counter.

Figure 12:
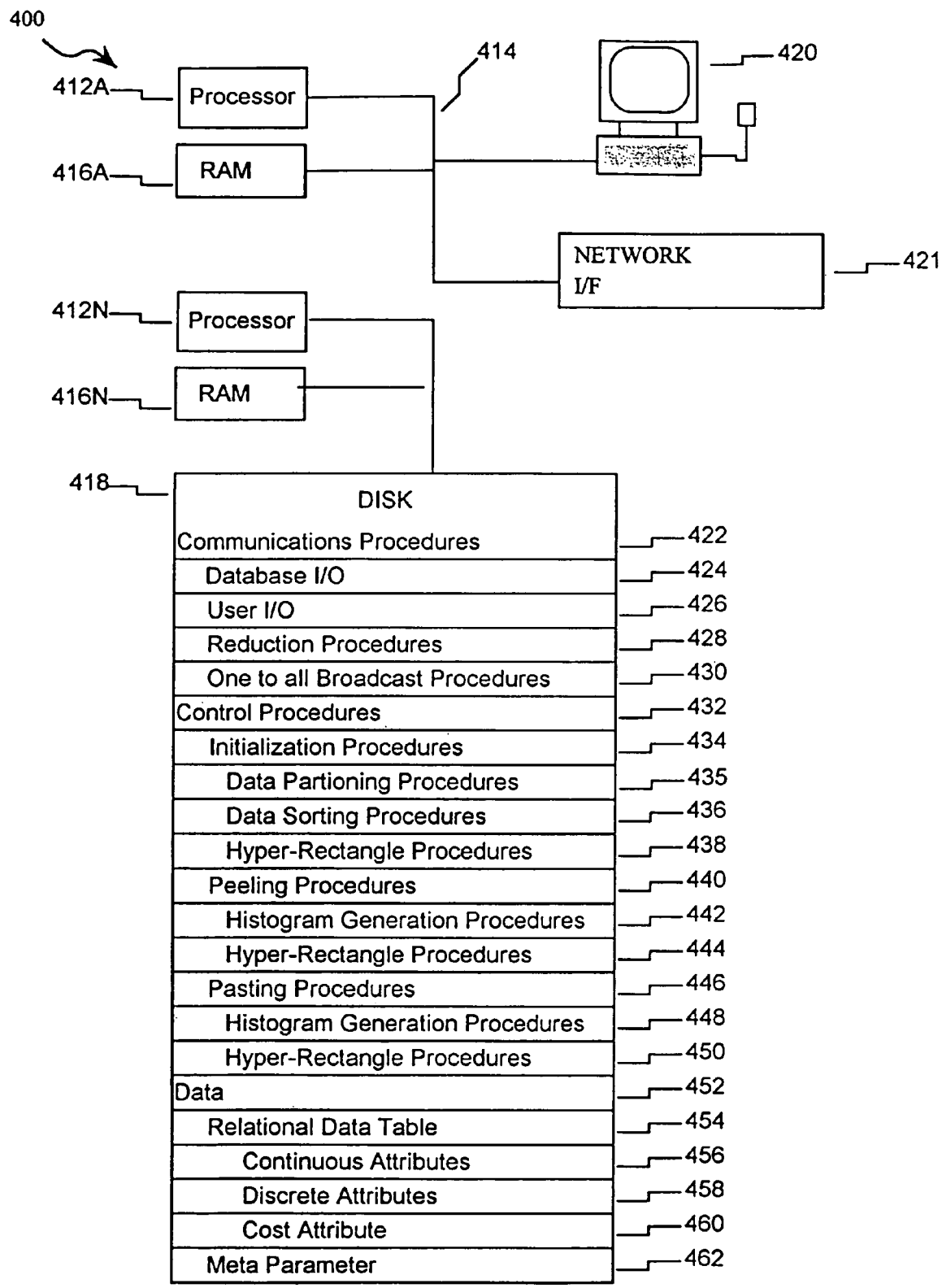
FIG. 12 depicts a parallel computer architecture according to an embodiment of the invention.
Figure 13:
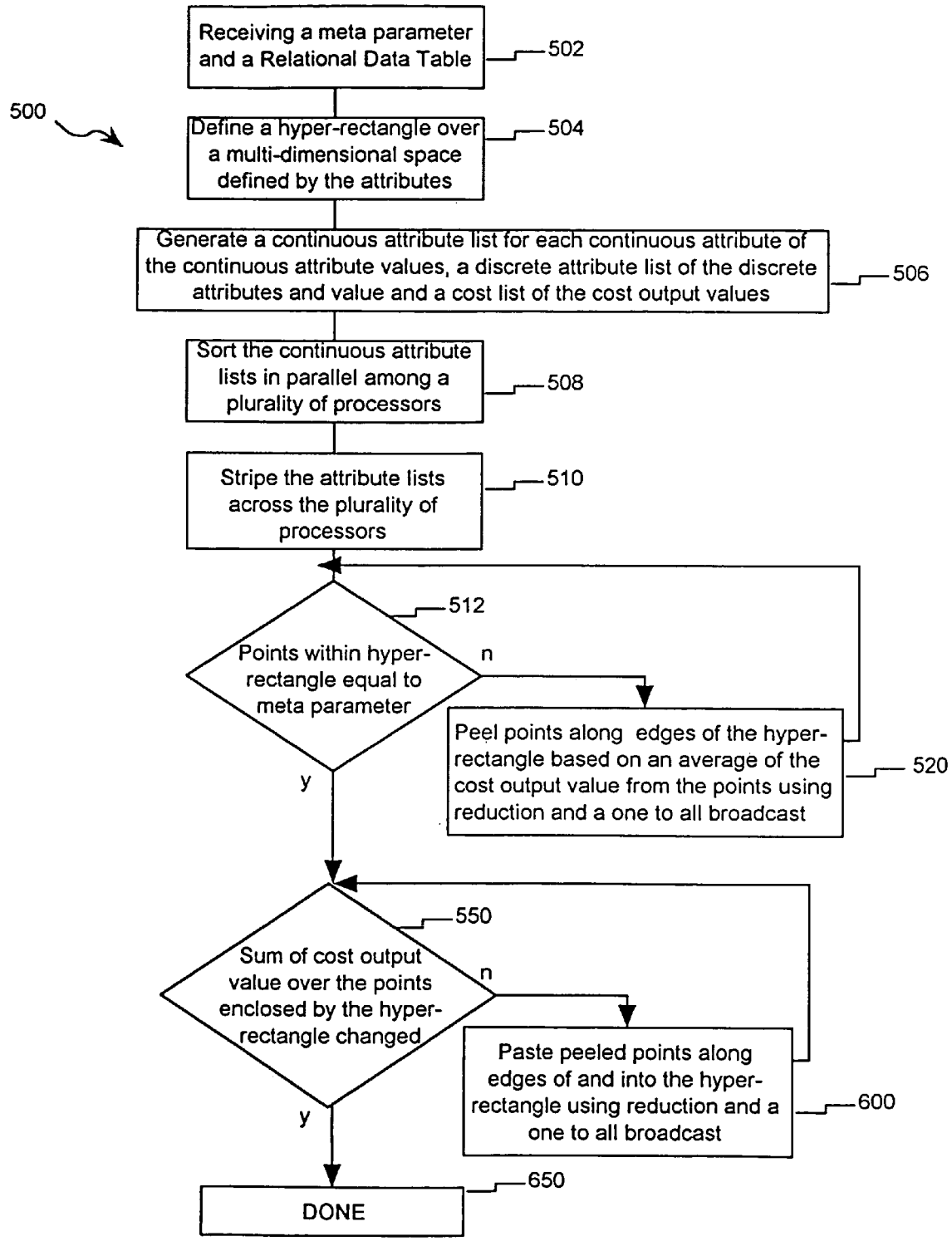
FIG. 13 is a flow chart depicting operation of the Patient Rule Induction Method in a parallel computer architecture.

A further embodiment of the invention is described with reference to FIGS. 12 and 13. FIG. 12 depicts a parallel architecture computer system 400 according to an embodiment of the invention. The computer system includes a plurality of processors 412A-412N coupled to a bus 414. A random access memory 416 for each processor 412 and a hard disk memory 418 are also coupled to the bus 414 and are accessible by the plurality of processors 412. The hard disk 418 is configured to store programs and data necessary for the invention, as described below. An optional user interface 420 is provided for input of raw data. In one embodiment, the input/output devices include a keyboard, mouse, and monitor. An optional network interface 421 is also provided. It should be appreciated that raw data may be entered in various different ways, for example via the user interface 18 or the network interface 20.

The hard disk 418 is configured to store the program and data in the computer system 10. The memory, including the RAM and the hard disk, is divided into three primary components: communications procedures 422, control procedures 432, and data 452. The communications procedures include routines 424-430 for identifying large disk resident data sets and providing communication among the plurality of processors. The control procedures include routines 434-450 that perform the invention's data analysis functions. The data portion creates indexes to an $A_c$ continuous attribute lists and a discrete attribute list of the relational data table 454, and stores a cost list, and a meta parameter 456 in main memory (RAM) 416. These routines are described in greater detail below.

Operation of the invention is described with reference to the FIG. 13 flowchart. At step 502, a meta parameter and a relational data table are received. As described above, the relational data table is includes $A_c$ continuous attributes, discrete attributes and a cost attribute. The cost attribute represents cost output values based on continuous attributes values and discrete attribute values as inputs. At step 504, a hyper-rectangle is defined by enclosing a multi-dimensional space defined by the continuous attribute values and the discrete attribute values. At step 506, the data is separated into $A_c+2$ lists. A list is generated for each continuous attribute to form $A_c$ continuous attribute lists containing the continuous attribute values A discrete attribute list containing the $A_d$ discrete attributes and the discrete attribute values. A cost attribute list containing the cost output values is stored in main memory. Each of the $A_c$ continuous attribute lists, the discrete attribute list and the cost attribute list also include a label. The label is an index of the tuple to which the respective attribute value belongs within the relational data table. The index allows the continuous attribute values and discrete attribute values to reference their respective tuple and cost output value. The lists also include a cost counter label. The cost counter is a count of the number of points of the tuple that are not enclosed within the hyper-rectangle as described above.

Figure 14:
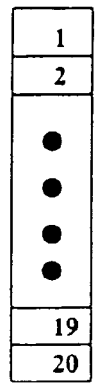
FIG. 14 depicts data redistribution among the plurality of processors using striping according to an embodiment of the invention.
Figure 14:
Figure 14:
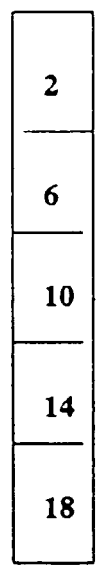
Figure 14:
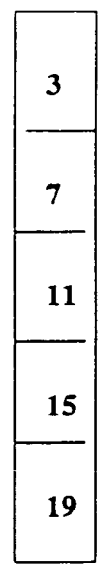
Figure 14:
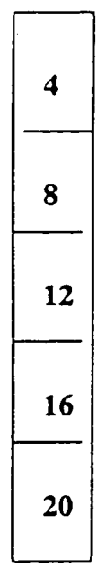

At step 508, the $A_c$ continuous attribute lists are sorted in parallel among the plurality of processors based on the continuous attribute values in each row of the cost attribute lists. At step 510, the attribute lists are stripe across the plurality of processors as depicted in FIG. 14. At steps 512 and 520, a plurality of points along edges of the hyper-rectangle are removed (peeled) based on an average of the cost output value from the plurality of points using reduction and a one to all broadcast with the plurality of processors. The points are repeatedly removed until a count of the points enclosed within the hyper-rectangle equals the meta parameter. Finally at steps 550 and 600, removed discrete attribute value points and the continuous attribute value points are added (pasted) along the edges of the hyper-rectangle until a sum of the cost output values over the multi-dimensional space enclosed by the hyper-rectangle changes using reduction and a one to all broadcast with the plurality of processors.

Some synchronization steps may be required for getting the exact fraction of points for the continuous attributes. This is due to possibility of some continuous attribute values in an attribute list no longer being present inside the hyper-rectangle. Details concerning the communication and synchronization among the plurality of processors will be apparent to those skilled in the art of parallel computer architectures and are therefore not set forth herein except as needed for a proper understanding of the invention. However, a reduction step for all the processors can be performed to get the average value for a particular attribute during the peeling phase. The best attribute can be selected for peeling. After the peeling has been performed the peeled transaction id's are transferred to each processor so that it can update the tags for its memory resident cost attribute list. Conventional reduction, implemented as a converse to the one to all broadcast, is well known in the field of parallel computing. (*Introduction to Parallel Computing: Design and Analysis of Algorithms* by Vipin Kumar, Ananth Grama, Anshul Gupta, and George Karypis Chapter 3, § 3.2.)

Figure 15:
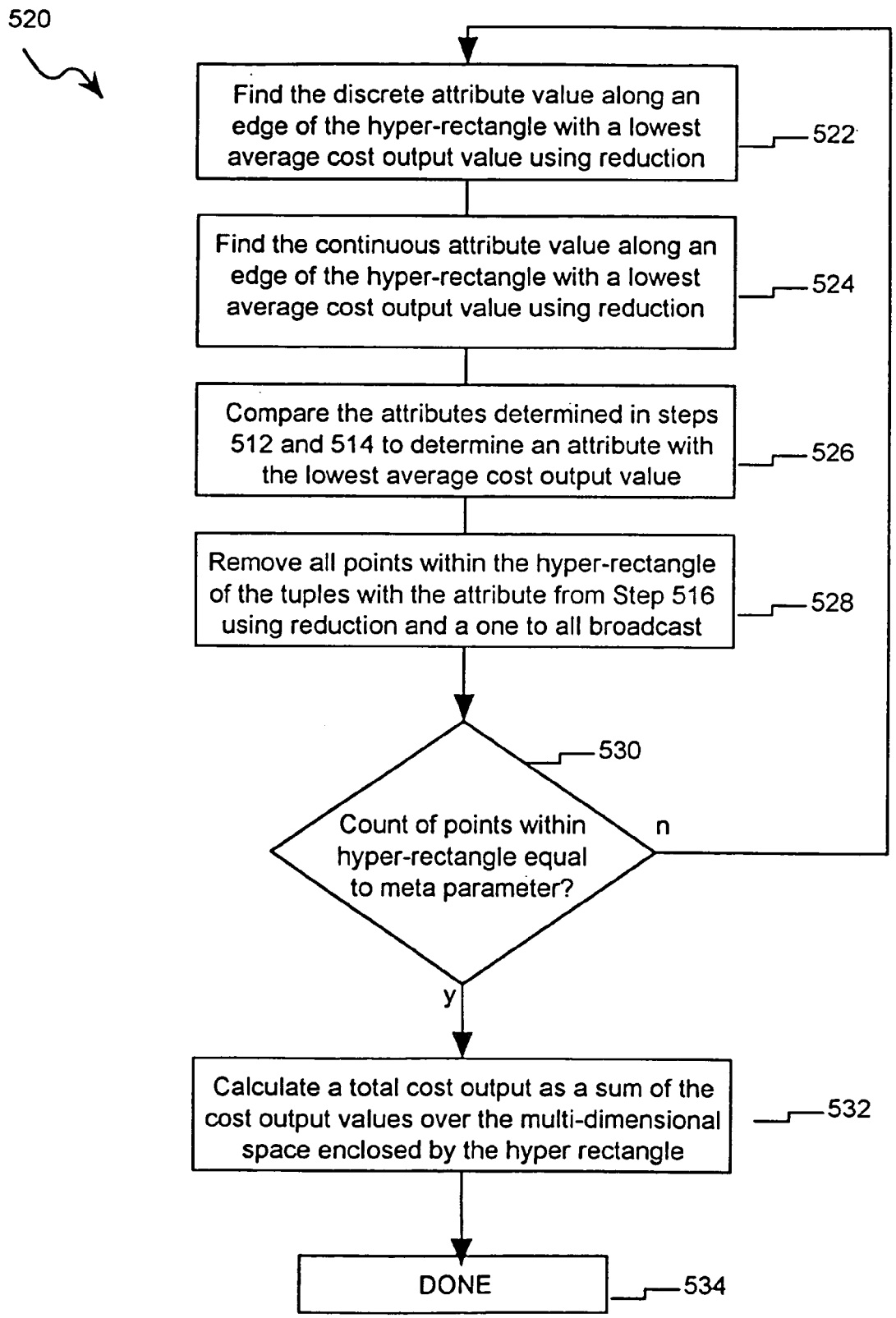
FIG. 15 depicts additional method steps for performing the peeling procedures according to a further embodiment of the invention.

FIG. 15 depicts additional methods steps for the peeling procedures 440 of step 520 according to a further embodiment of the invention. At step 522, a discrete attribute value enclosed within the plurality of points along an edge of the hyper-rectangle with a lowest average cost output value is found using reduction among the processors. At step 524, the continuous attribute value enclosed within the plurality of points along an edge of the hyper-rectangle with a lowest average cost output value is found using reduction. At step 526, the lowest average cost output value determined in step 522 is compared with the lowest average cost output value determined in step 524 to determine an attribute with the lowest average cost output value. At step 528, all continuous attribute value points and all discrete attribute value points of the tuples containing the attribute determined in step 526 are removed (peeled) from the hyper-rectangle using a one to all broadcast between the processors. At step 530, steps 522 to 528 are repeated until the count of the points within the hyper-rectangle equals $\beta_0$.

Finally at step 532, a total cost output is calculated. The total cost output is a sum of the cost output values over the multi-dimensional space enclosed by the hyper-rectangle. Although the peeling procedure described above is maximizing the points enclosed by the hyper-rectangle, the points enclosed by the hyper-rectangle could be minimized as well. As describe above, the lowest average cost output value of step 520 can be calculated using a plurality of discrete histograms.

Figure 16:
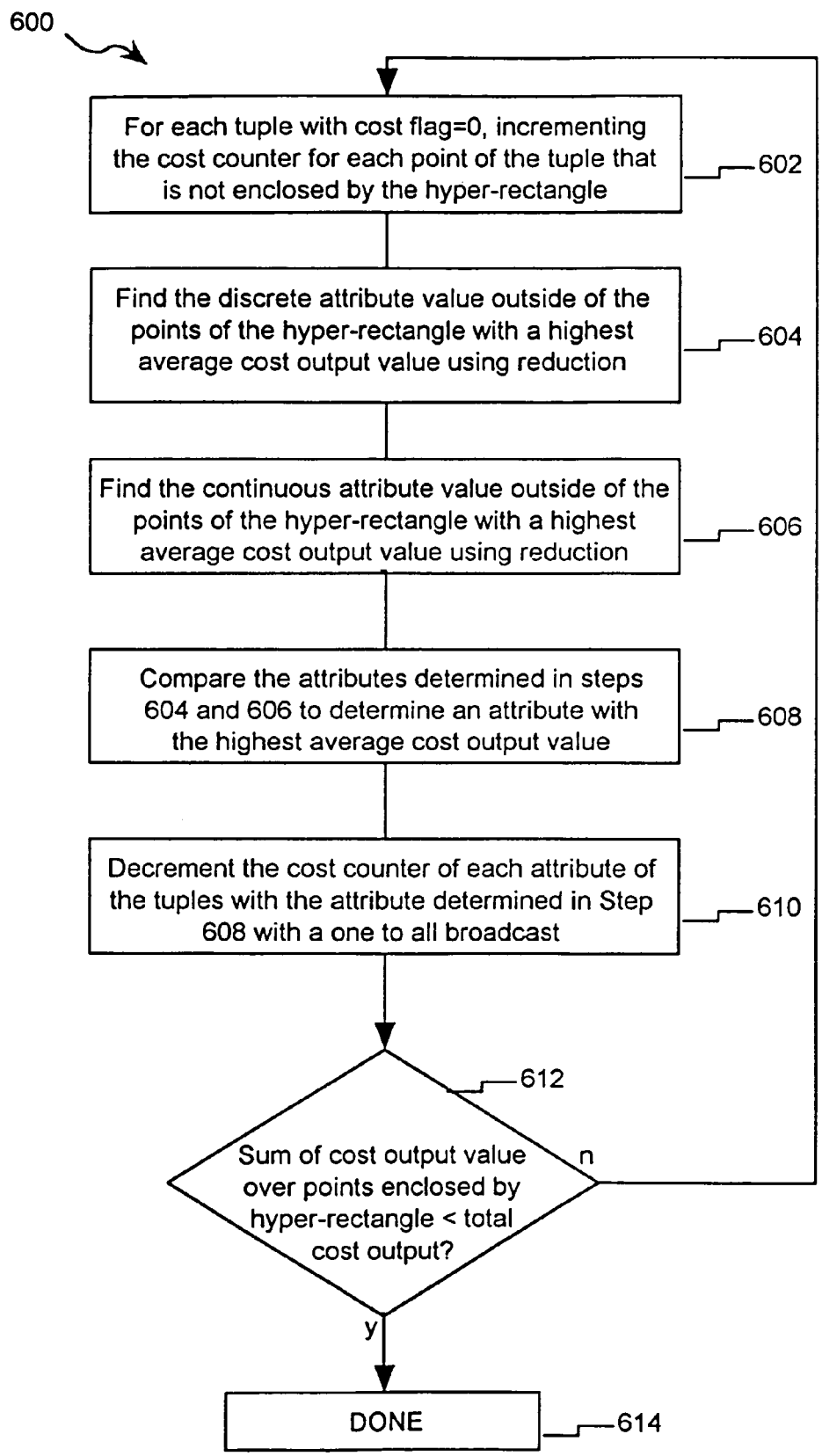
FIG. 16 depicts additional method steps for performing the pasting procedures according to a further embodiment of the invention.

FIG. 16 depicts additional methods steps for performing the pasting procedures 440 of step 600 according to a further embodiment of the invention. At step 602, for each tuple with the cost flag set to zero, incrementing the cost counter for each point belonging to the tuple that is not enclosed with the hyper-rectangle. At step 604, the discrete attribute value outside of the points enclosed by the hyper-rectangle with a highest average cost output value is determined using reduction and a one to all broadcast between the processors. At step 606, the continuous attribute value outside of the points enclosed by the hyper-rectangle with a highest average cost output value is determined using reduction and a one to all broadcast between the processors. At step 608, the highest average cost output value determined in step 604 is compared with the highest average cost output value determined in step 606 to find an attribute with the highest average cost output value. Finally at step 300, the cost counter for all continuous attribute value points and all discrete attribute value points belonging to the tuples containing the attribute determined in step 608 are decremented using a one to all broadcast between the processors. Attributes with the cost counter equal to zero are enclosed within the hyper-rectangle. At step 612, steps 602 to 610 are repeated until a sum of the cost output value over the plurality of points enclosed by the hyper-rectangle is less than the total cost output. This pasting procedure ensure a more through representation of high value points. As describe above, the highest average cost output value of step 604 is calculated using a plurality of discrete histograms.

Figure 17:
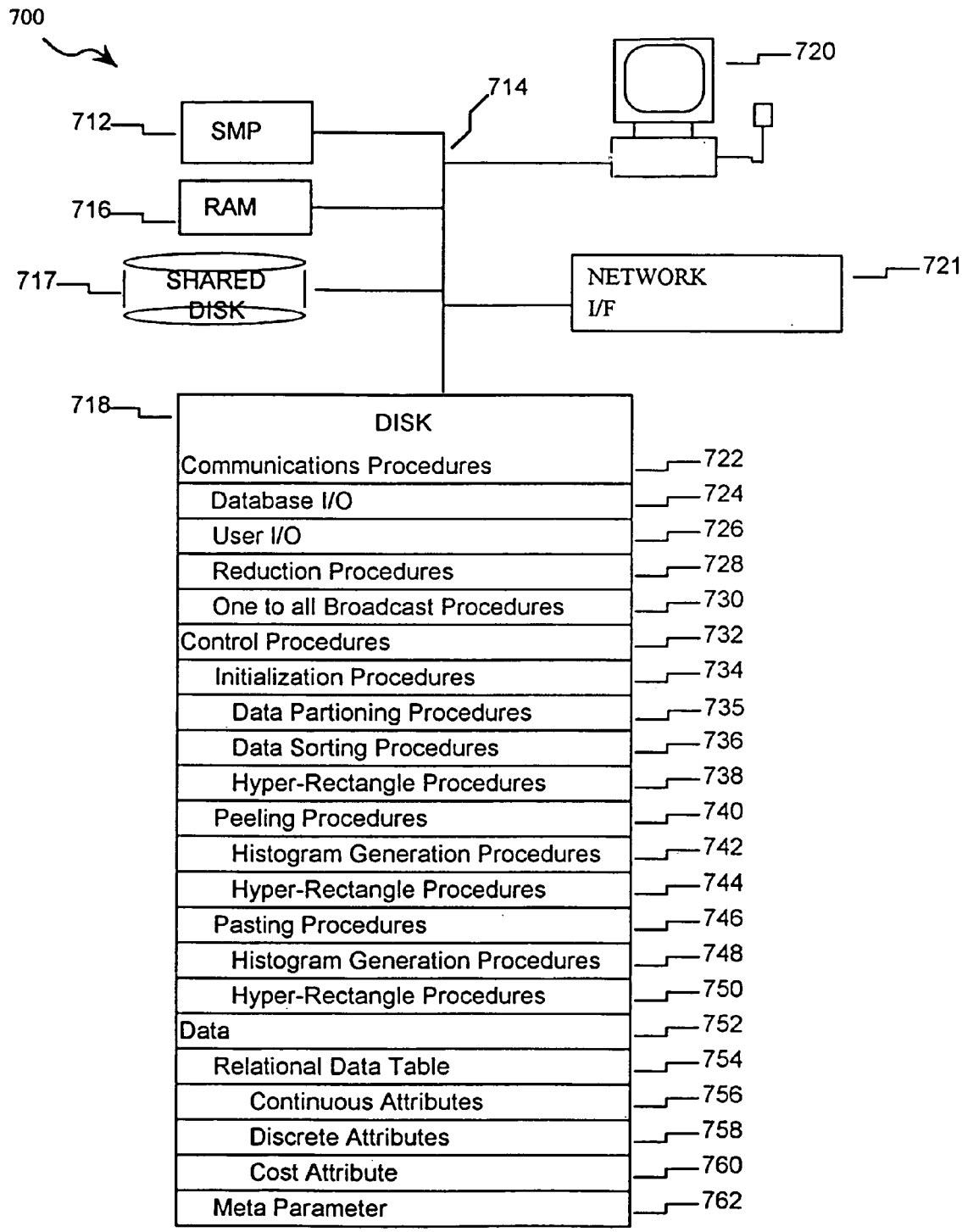
FIG. 17 depicts a symmetric multi-processor computer system according to an embodiment of the invention.
Figure 18:
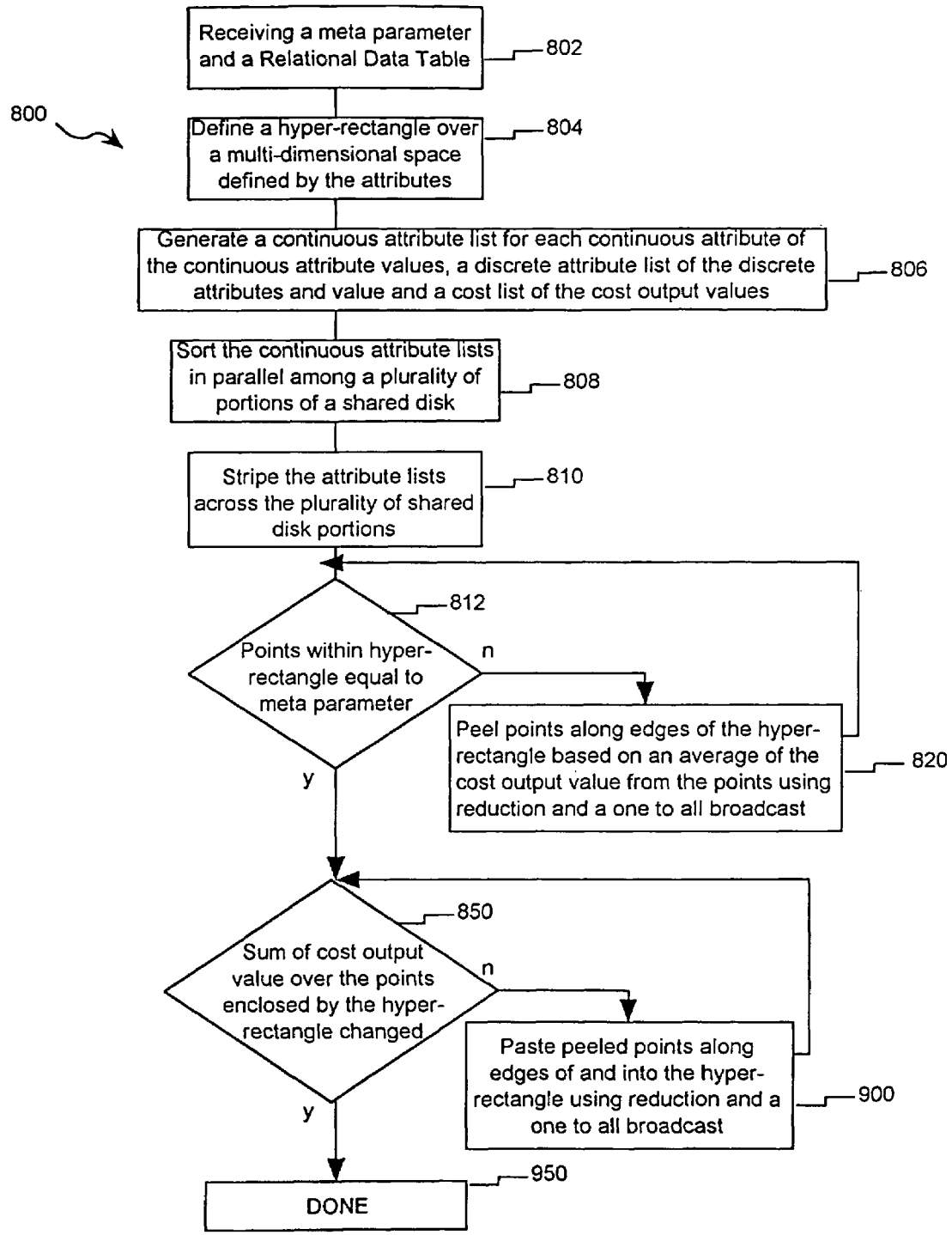
FIG. 18 is a flow chart depicting operation of the Patient Rule Induction Method on a symmetric multi-processor computer architecture.

A further embodiment of the invention is described with reference to FIGS. 17 and 18. FIG. 17 depicts a symmetric multi-processor computer system 700 according to an embodiment of the invention. The symmetric multi-processor (SMP) 712 coupled to a bus 714. A random access memory 716 and a share hard disk memory 717 are also coupled to the bus 714. The shared disk 717 is partitioned into a plurality of portion that are accessible by the symmetric multi-processors 712. The main memory (RAM) 716 is configured to store programs and data necessary for the invention, as described below. An optional user interface 718 is provided for input of raw data. In one embodiment, the input/output devices include a keyboard, mouse, and monitor. An optional network interface 721 is also provided. It should be appreciated that raw data may be entered in various different ways, for example via the user interface 720 or the network interface 721.

The hard disk 718 is configured to store the program and data in the computer system 700. The memory, including the RAM and the hard disk, is divided into three primary components: communications procedures 722, control procedures 732, and data 752. The communications procedures include routines 724-730 for identifying large disk resident data sets and providing communication for the symmetric multi-processors 712. The control procedures include routines 735-754 that perform the invention's data analysis functions. The data portion creates indexes to an $A_c$ continuous attribute lists and a discrete attribute list of the relational data table 754, and stores a cost list, and a meta parameter 762 in main memory (RAM) 716. These routines are described in greater detail below.

Operation of the invention is described with reference to the FIG. 18 flowchart. At step 802, a meta parameter and a relational data table are received. As describe above, the relational data table is includes $A_c$ continuous attributes, discrete attributes and a cost attribute. The cost attribute represents cost output values based on continuous attributes values and discrete attribute values as inputs. At step 804, a hyper-rectangle is defined by enclosing a multi-dimensional space defined by the continuous attribute values and the discrete attribute values. At step 806, the data is separated into $A_c+2$ lists. A list is generated for each continuous attribute to form $A_c$ continuous attribute lists containing the continuous attribute values A discrete attribute list containing the $A_d$ discrete attributes and the discrete attribute values. A cost attribute list containing the cost output values is stored in main memory. Each of the $A_c$ continuous attribute lists, the discrete attribute list and the cost attribute list also include a label. The label is an index of the tuple to which the respective attribute value belongs within the relational data table. The index allows the continuous attribute values and discrete attribute values to reference their respective tuple and cost output value. The lists also include a cost counter label. The cost counter is a count of the number of points of the tuple that are not enclosed within the hyper-rectangle as described above.

At step 808, the $A_c$ continuous attribute lists are sorted in parallel among the plurality of shared disk portions based on the continuous attribute values in each row of the cost attribute lists. At step 810, the attribute lists are stripe across the plurality of shared disk portions as depicted in FIG. 14. At steps 812 and 820, a plurality of points along edges of the hyper-rectangle are removed (peeled) based on an average of the cost output value from the plurality of points using reduction and a one to all broadcast within the symmetric multi-processors. The points are repeatedly removed until a count of the points enclosed within the hyper-rectangle equals the meta parameter. Finally at steps 850 and 900, removed discrete attribute value points and the continuous attribute value points are added (pasted) along the edges of the hyper-rectangle until a sum of the cost output values over the multi-dimensional space enclosed by the hyper-rectangle changes using reduction and a one to all broadcast within the symmetric multi-processors.

Figure 19:
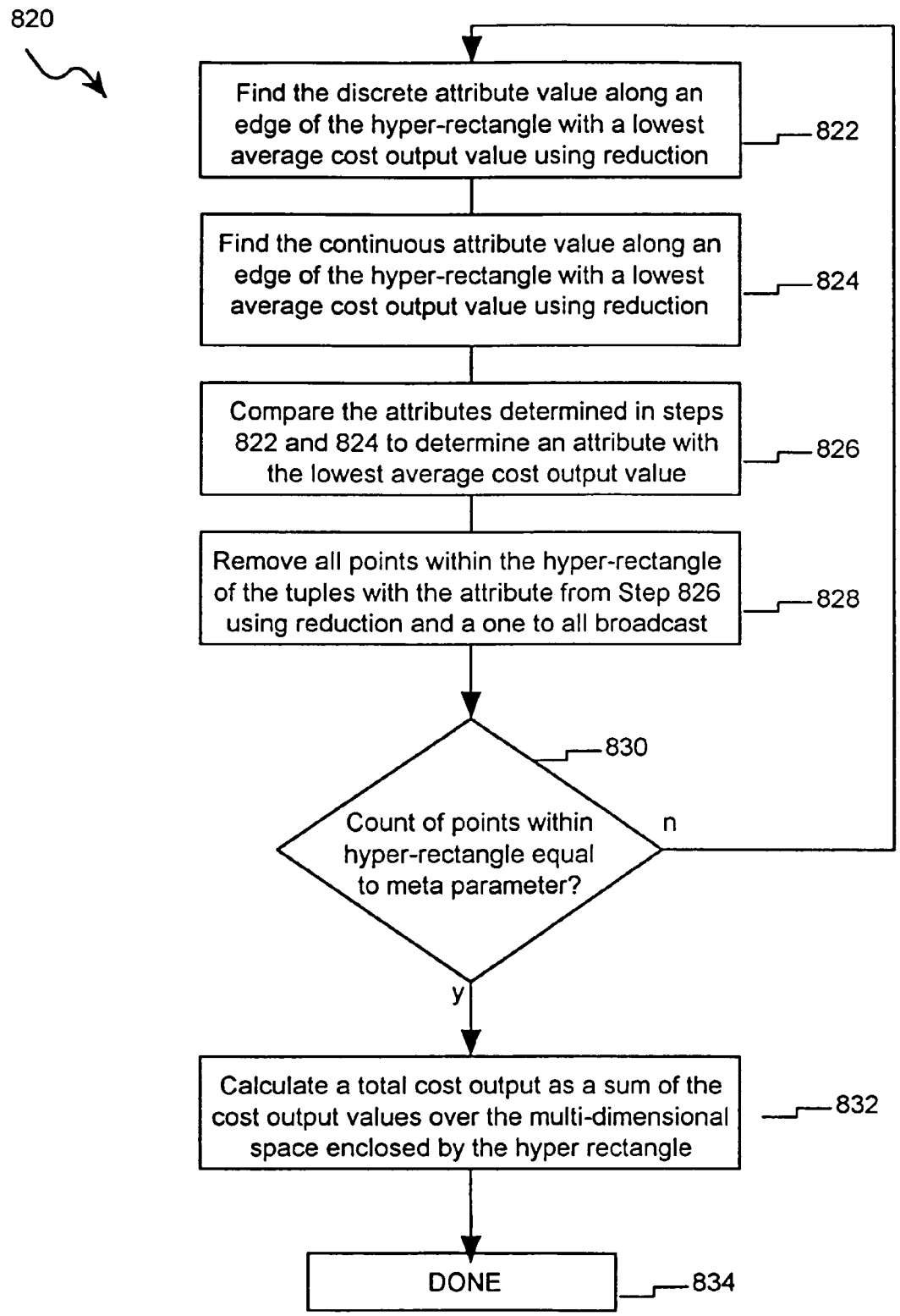
FIG. 19 depicts additional method steps for performing the peeling procedures according to a further embodiment of the invention.

FIG. 19 depicts additional methods steps for the peeling procedures 740 of step 820 according to a further embodiment of the invention. At step 822, a discrete attribute value enclosed within the plurality of points along an edge of the hyper-rectangle with a lowest average cost output value is found using reduction within the symmetric multi-processor. At step 824, the continuous attribute value enclosed within the plurality of points along an edge of the hyper-rectangle with a lowest average cost output value is found using reduction. At step 826, the lowest average cost output value determined in step 822 is compared with the lowest average cost output value determined in step 824 to determine an attribute with the lowest average cost output value. At step 828, all continuous attribute value points and all discrete attribute value points of the tuples containing the attribute determined in step 826 are removed (peeled) from the hyper-rectangle using a one to all broadcast within the symmetric multi-processors. At step 830, steps 822 to 828 are repeated until the count of the points within the hyper-rectangle equals $\beta_0$. Finally at step 832, the total cost output is calculated as described above. As describe above, the lowest average cost output value of step 520 can be calculated using a plurality of discrete histograms.

Figure 20:
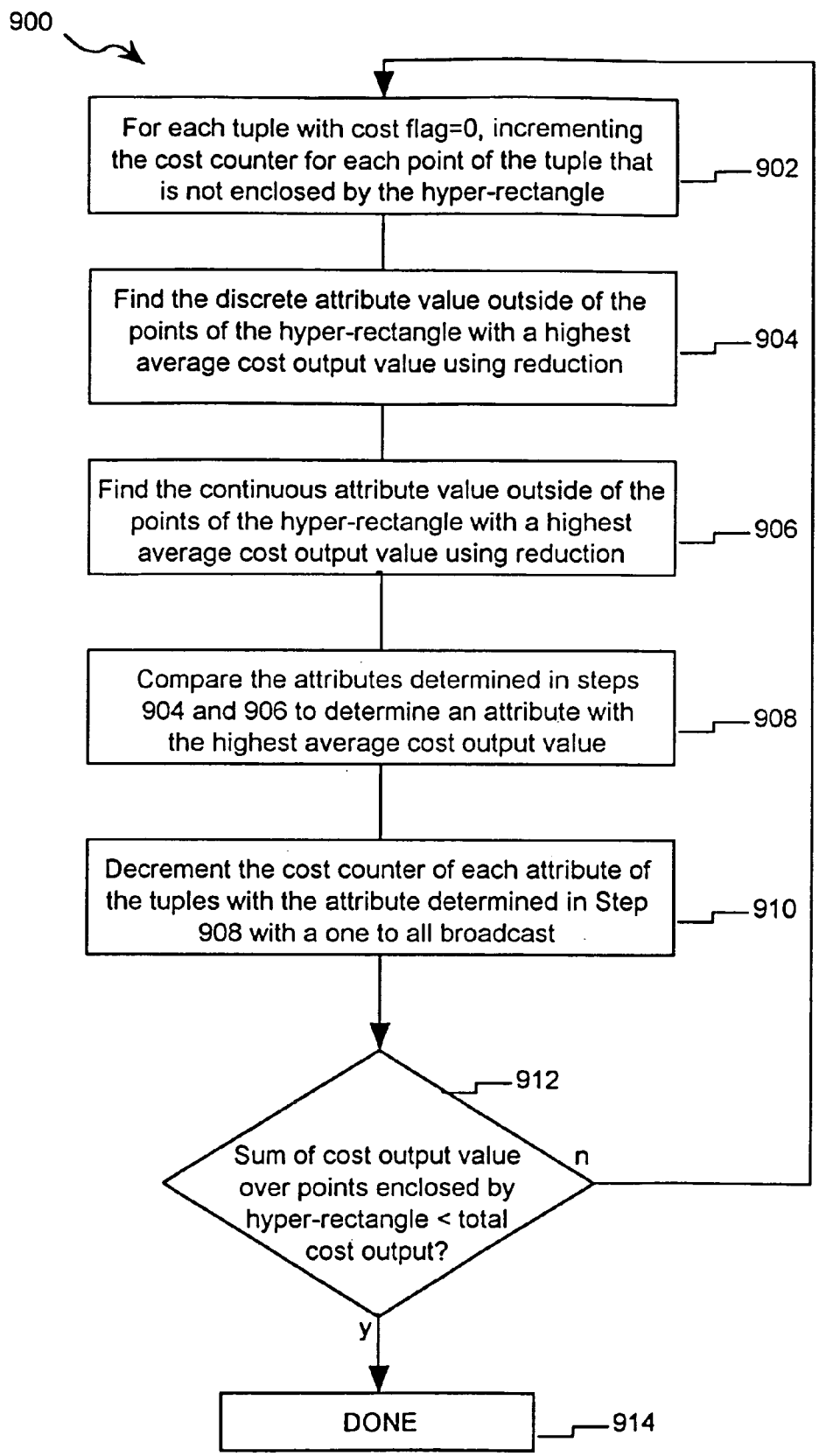
FIG. 20 depicts additional method steps for performing the pasting procedures according to a further embodiment of the invention.

FIG. 20 depicts additional methods steps for performing the pasting procedures 746 of step 900 according to a further embodiment of the invention. At step 902, for each tuple with the cost flag set to zero, incrementing the cost counter for each point belonging to the tuple that is not enclosed with the hyper-rectangle using a one to all broadcast within the symmetric multi-processors. At step 904, the discrete attribute value outside of the points enclosed by the hyper-rectangle with a highest average cost output value is determined using reduction and a one to all broadcast within the symmetric multi-processors. At step 906, the continuous attribute value outside of the points enclosed by the hyper-rectangle with a highest average cost output value is determined using reduction and a one to all broadcast within the symmetric multi-processors. At step 908, the highest average cost output value determined in step 904 is compared with the highest average cost output value determined in step 906 to find an attribute with the highest average cost output value. Finally at step 910, the cost counter for all continuous attribute value points and all discrete attribute value points belonging to the tuples containing the attribute determined in step 908 are decremented using a one to all broadcast within the symmetric multi-processors. Attributes with the cost counter equal to zero are enclosed within the hyper-rectangle. At step 912, steps 902 to 910 are repeated until a sum of the cost output value over the plurality of points enclosed by the hyper-rectangle is less than the total cost output. This pasting procedure ensure a more through representation of high value points. As describe above, the highest average cost output value of step 904 is calculated using a plurality of discrete histograms.

Exemplary embodiments have been described with reference to specific configurations. Those skilled in the art will appreciate that various changes and modifications can be made while remaining within the scope of the claims. It is to be understood that even though numerous characteristics and advantages of various embodiments of the present invention have been set forth in the foregoing description, together with details of the structure and function of various embodiments of the invention, this disclosure is illustrative only, and changes may be made in detail, especially in matters of structure and arrangement of parts within the principles of the present invention to the full extent indicated by the broad general meaning of the terms in which the appended claims are expressed.

For example, it is within the contemplation of the present invention to practice the invention with a conventional computer without departing from the scope of the invention. Moreover, teaching of the present invention are not limited to maximization of some output value over a multi-dimensional space of input values. The invention may be practiced by minimizing the points over the multi-dimensional space without departing from the scope of the invention.

The invention provides many advantages over known techniques. The present invention includes the ability to analyze large, disk resident data sets without having to load the data set into main memory. In addition, the invention can be practiced on a parallel computer architecture or a symmetric multi-processor architecture to improve performance. Moreover, the memory requirements of the invention are only limited by the size of the cost attribute sought to be maximized or minimized.

Having disclosed exemplary embodiments and the best mode, modifications and variations may be made to the disclosed embodiments while remaining within the scope of the invention as defined by the following claims.

What is claimed is:

1. In a computer system having a large disk resident data set, a method of analyzing the disk resident data set using a patient rule induction method (PRIM), the method comprising steps of:
   (a) receiving a meta parameter and a relational data table comprised of continuous attributes, discrete attributes and a cost attribute, wherein the cost attribute represents cost output values based on continuous attributes values and discrete attribute values as inputs;
   (b) defining a hyper-rectangle enclosing a multi-dimensional space defined by the continuous attribute values and the discrete attribute values, wherein the continuous attribute values and the discrete attribute values are represented as points within the multi-dimensional space, further including steps of:
      (i) separating the data into at least three lists, including a continuous attribute list for each continuous attribute containing the continuous attribute values, a discrete attribute list containing the discrete attributes and the discrete attribute values, and a cost attribute list containing the cost output values;
      (ii) adding a label to each of the continuous attribute lists, the discrete attribute list and the cost attribute list, such that the label is an index of a tuple to which the respective attribute value belongs within the relational data table;
      (iii) sorting the continuous attribute lists based on a continuous attribute value in each row of the continuous attribute lists; and
      (iv) adding a label to the cost list, such that the label is a cost flag that indicates whether the tuple containing the cost output value is enclosed within the hyper-rectangle, such that the cost flag is initially set to one;
   (c) removing a plurality of points along edges of the hyper-rectangle based on an average of the cost output value from the plurality of points until a count of the points enclosed within the hyper-rectangle equals the meta parameter; and
   (d) adding removed discrete attribute value points and the continuous attribute value points along the edges of the hyper-rectangle until a sum of the cost output values over the multi-dimensional space enclosed by the hyper-rectangle changes.

2. The method of claim 1, wherein the continuous attributes are $A_c$ continuous attributes, the discrete attributes are $A_d$ discrete attributes and the meta parameter is $\beta_0$, further wherein the data of step (b)(i) is separated into $A_c+2$ lists, such that at least $A_c$ continuous attribute lists are formed.

3. The method of claim 2, wherein, step (c) further including steps of:
   (c)(i) determining the discrete attribute value enclosed within the plurality of points along an edge of the hyper-rectangle with a lowest average cost output value;
   (c)(ii) determining the continuous attribute value enclosed within the plurality of points along an edge of the hyper-rectangle with a lowest average cost output value;
   (c)(iii) comparing the lowest average cost output value determined in step (c)(i) with the lowest average cost output value determined in step (c)(ii) to determine an attribute with the lowest average cost output value; and
   (c)(iv) removing all continuous attribute value points and all discrete attribute value points of the tuples containing the attribute determined in step (c)(iii) from the hyper-rectangle; and
   (c)(v) repeating steps (c)(i) to (c)(iv) until the count of the points within the hyper-rectangle equals $\beta_0$.

4. The method of claim 3, wherein, step (c)(i) further including steps of:
   1) generating $A_d$ discrete histograms, one for each discrete attribute containing the discrete attribute value and an average of the cost output value for each tuple containing the discrete attribute value; and
   2) comparing the average cost output value for each discrete attribute value to determine the discrete attribute value with the lowest average cost output value.

5. The method of claim 4, wherein step 1) further includes a step of:

assigning a code to the discrete attribute list, wherein the discrete attribute list is sorted based on the assigned code in order to optimize step (c), such that the discrete attribute values are ground together according to their discrete attribute.

6. The method of claim 3, wherein, each continuous attribute list is sorted in increasing order with a start pointer to a first row in each continuous attribute list, and a second continuous attribute list is sorted in decreasing order with an end pointer to a first row in each second continuous attribute list, step (c)(ii) further including steps of:

1) marking a start cutoff value in each of the $A_c$ continuous attribute lists based on a count of the tuples containing the discrete attribute value determined in step (c)(i) and enclosed within the hyper-rectangle;
2) marking an end cutoff value in each of the second continuous attribute lists based on the count of the tuples containing the discrete attribute value determined in step (c)(i) and enclosed within the hyper-rectangle;
3) determining a start cost average value for each continuous output value between the start pointer and the cutoff value for each of the $A_c$ cost attribute lists;
4) determining an end cost average value for each continuous output value between the cutoff value and the end pointer for each of the second cost attribute lists;
5) generating $A_c$ continuous histograms, each containing the continuous attribute and the average cost output value, wherein the average cost output value is a lesser of the start cost average value and the end cost average value; and
6) comparing the average cost output value for each continuous histogram to determine the continuous attribute value with the lowest average cost output value.

7. The method of claim 6, wherein the discrete attribute list is sorted based on an assigned code thereby grouping the discrete attribute values according to their discrete attribute, step (c)(iv) further includes steps of:

when the attribute determined in step (c)(iii) is a continuous attribute,
1) when the start cost average value is less than the end cost average value, setting the cost flag equal to zero for each continuous attribute value between the start pointer and the start cutoff value using the index of the continuous attribute value to reference the cost flag,
2) setting the start pointer equal to the start cutoff value;
3) when the end cost average value is less than the start cost average value, setting the cost flag equal to zero for each continuous attribute value between the end cutoff value and the end pointer the using the index of the continuous attribute value to reference the cost flag,
4) setting the end pointer equal to the end cutoff value;
when the attribute determined in step (c)(iii) is a discrete attribute; and
5) setting the cost flag equal to zero for each discrete attribute value equal to the attribute determined in step (c)(iii) using the index of the discrete attribute value to reference the cost flag.

8. The method of claim 2, wherein a total cost output is a sum of the cost output values over the multidimensional space enclosed by the hyper-rectangle following step (c), and the cost attribute list includes a cost counter, step (d) further including steps of:

(d)(i) for each tuple with the cost flag set to zero, incrementing the cost counter for each point belonging to the tuple that is not enclosed with the hyper-rectangle;
(d)(ii) determining the discrete attribute value outside of the points enclosed by the hyper-rectangle with a highest average cost output value;
(d)(iii) determining the continuous attribute value outside of the points enclosed by the hyper-rectangle with a highest average cost output value;
(d)(iv) comparing the highest average cost output value determined in step (d)(ii) with the highest average cost output value determined in step (d)(iii) to determine an attribute with the highest average cost output value;
(d)(v) decrementing the cost counter for all continuous attribute value points and all discrete attribute value points belonging to the tuples containing the attribute determined in step (d)(iv), such that attributes with the cost counter equal to zero are enclosed within the hyper-rectangle; and
(d)(vi) repeating steps (d)(i) to (d)(v) until a sum of the cost output value over the plurality of points enclosed by the hyper-rectangle is less than the total cost output.

9. The method of claim 8, wherein, step (d)(ii) further including steps of:

1) generating $A_d$ discrete histograms, one for each discrete attribute containing the discrete attribute value and an average of the cost output value for each tuple containing the discrete attribute value; and
2) comparing the average cost output value for each discrete attribute value to determine the discrete attribute value with the highest average cost output value.

10. The method of claim 8, wherein the $A_c$ continuous attribute lists are sorted in increasing order and each contain a start pointer and an end pointer, such that the continuous attribute values there between are enclosed within the hyper-rectangle, step (d)(iii) further including steps of:

1) sorting the continuous attribute values in the $A_c$ continuous attributes lists between a first row in the $A_c$ continuous attributes lists and the start pointer in decreasing order;
2) marking a start cutoff value in each of the $A_c$ continuous attribute lists based on a count of the tuples containing the discrete attribute value determined in step (d)(ii) and enclosed within the hyper-rectangle;
3) marking an end cutoff value in each of the $A_c$ continuous attribute lists based on the count of the tuples containing the discrete attribute value determined in step (d)(ii) and enclosed within the hyper-rectangle;
4) determining a start cost average value for each continuous output value between the start pointer and the cutoff value for each of the $A_c$ continuous attribute lists;
5) determining an end cost average value for each continuous output value between the end pointer and the cutoff value for each of the $A_c$ continuous attribute lists;
6) generating $A_c$ continuous histograms, each containing the continuous attribute and the average cost output value, wherein the average cost output value is a greater of the start cost average value and the end cost average value; and 7) comparing the average cost output value for each continuous histogram to determine the continuous attribute value with the highest average cost output value.

11. The method of claim 10, wherein the discrete attribute list is sorted based on an assigned code thereby grouping the discrete attribute values according to their discrete attribute, step (d)(v) further includes steps of:
when the attribute determined in step (d)(iv) is a continuous attribute,
1) when the start cost average value is less than the end cost average value, decrementing the cost counter for each continuous attribute value between the start cutoff value and the start pointer using the index of the continuous attribute value to reference the cost counter;
2) setting the start pointer equal to the start cutoff value;
when the attribute determined in step (d)(iv) is a discrete attribute; and
3) decrementing the cost counter for each discrete attribute value equal to the attribute determined in step (d)(iv) using the index of the discrete attribute value to reference the cost counter.

12. In a parallel architecture computer system having a large disk resident data set, a method of analyzing the disk resident data set in parallel using a patient rule induction method (PRIM), comprising steps of:
(a) receiving a relational table of data comprised of $A_c$ continuous attributes, $A_d$ discrete attributes, a meta parameter $\beta_0$ and a cost attribute, wherein the cost attribute represents cost output values based on continuous attributes values and discrete attribute values as inputs;
(b) defining a hyper-rectangle enclosing a multi-dimensional space defined by the continuous attribute values and the discrete attribute values, wherein the continuous attribute values and the discrete attribute values are represented as points within multi-dimensional space;
(c) separating the data into $A_c$+2 lists, such that a list is generated for each continuous attribute to form $A_c$ continuous attribute lists containing the continuous attribute values, a discrete attribute list containing the $A_d$ discrete attributes and the discrete attribute values and a cost attribute list containing the cost output values;
(d) sorting the $A_c$ continuous attribute lists in parallel among a plurality of processors based on a continuous attribute value in each row of the $A_c$ continuous attribute lists;
(e) striping the $A_c$ continuous attribute lists and the discrete attribute lists across the plurality of processor, wherein each processor contains a copy of the cost attribute list;
(f) removing a plurality of points along edges of the hyper-rectangle using reduction and a one to all broadcast based on an average of the cost output value from the plurality of points until a count of the points enclosed within the hyper-rectangle equals the meta parameter; and
(g) adding removed discrete attribute value points and the continuous attribute value points along the edges of the hyper-rectangle using reduction and a one to all broadcast until a sum of the cost output values over the multi-dimensional space enclosed by the hyper-rectangle changes.

13. The method of claim 12, wherein step (c) further including steps of:
(c)(i) adding a label to each of the $A_c$ continuous attribute lists, the discrete attribute list and the cost attribute list, such that the label is an index of a tuple to which the respective attribute belongs within the relational data table;
(c)(ii) adding a label to the cost list, such that the label is a cost flag that indicates whether the tuple containing the cost output value is enclosed within the hyper-rectangle, such that the cost flag is initially set to one.

14. The method of claim 13, wherein, step (f) further including steps of:
(f)(i) determining the discrete attribute value enclosed within the plurality of points along an edge of the hyper-rectangle with a lowest average cost output value using reduction;
(f)(ii) determining the continuous attribute value enclosed within the plurality of points along an edge of the hyper-rectangle with a lowest average cost output value using reduction;
(f)(iii) comparing the lowest average cost output value determined in step (f)(i) with the lowest average cost output value determined in step (f)(ii) to determine an attribute with the lowest average cost output value;
(f)(iv) removing all continuous attribute value points and all discrete attribute value points of the tuples containing the attribute determined in step (c)(iii) from the hyper-rectangle by setting the cost flag to zero using the index of the attribute to reference the cost flag in the cost list contained in each of the plurality of processors using the one to all broadcast; and
(f)(v) repeating steps (f)(i) to (f)(iv) until the count of the points within the hyper-rectangle equals $\beta_0$.

15. The method of claim 14, wherein a total cost output is a sum of the cost output values over the multidimensional space enclosed by the hyper-rectangle following step (f), and the cost attribute list includes a cost counter, step (g) further including steps of:
(g)(i) for each tuple with the cost flag set to zero, incrementing the cost counter for each point belonging to the tuple that is not enclosed with the hyper-rectangle among each of the plurality of processors;
(g)(ii) determining the discrete attribute value outside of the points enclosed by the hyper-rectangle with a highest average cost output value using reduction;
(g)(iii) determining the continuous attribute value outside of the points enclosed by the hyper-rectangle with a highest average cost output value using reduction;
(g)(iv) comparing the highest average cost output value determined in step (g)(ii) with the highest average cost output value determined in step (g)(iii) and determine which attribute with the highest average cost output value;
(g)(v) decrementing the cost counter for all continuous attribute value points and all discrete attribute value points belonging to the tuples containing the attribute determined in step (g)(iv) using the index of the attribute to reference the cost flag in the cost list contained in each of the plurality of processors using the one to all broadcast, such that attributes with the cost counter equal to zero are enclosed within the hyper-rectangle; and
(g)(vi) repeating steps (g)(i) to (g)(v) until a sum of the cost output value over the plurality of points enclosed by the hyper-rectangle is less than the total cost output.

16. In a symmetric multi-processor architecture computer system having a large disk resident data set, a method of analyzing the disk resident data set in parallel using a patient rule induction method (PRIM), comprising steps of:
(a) receiving a relational table of data comprised of $A_c$ continuous attributes, $A_d$ discrete attributes, a meta parameter $\beta_0$ and a cost attribute, wherein the cost attribute represents cost output values based on continuous attributes values and discrete attribute values as inputs;
(b) defining a hyper-rectangle enclosing a multi-dimensional space defined by the continuous attribute values and the discrete attribute values, wherein the continuous attribute values and the discrete attribute values are represented as points within multi-dimensional space;
(c) separating the data into $A_c$+2 lists, such that a list is generated for each continuous attribute to form $A_c$ continuous attribute lists containing the continuous attribute values, a discrete attribute list containing the $A_d$ discrete attributes and the discrete attribute values and a cost attribute list containing the cost output values;
(d) sorting the $A_c$ continuous attribute lists in parallel based on a continuous attribute value in each row of the $A_c$ continuous attribute lists;
(e) striping the $A_c$ continuous attribute lists and the discrete attribute lists over a plurality of portions of a shared disk, wherein each portion of the shared disk contains a copy of the cost attribute list;
(f) removing a plurality of points along edges of the hyper-rectangle using reduction and a one to all broadcast based on an average of the cost output value from the plurality of points until a count of the points enclosed within the hyper-rectangle equals the meta parameter; and
(g) adding removed discrete attribute value points and the continuous attribute value points along the edges of the hyper-rectangle using reduction and a one to all broadcast until a sum of the cost output values over the multi-dimensional space enclosed by the hyper-rectangle changes.

17. The method of claim 16, wherein, step (c) further including steps of:
(c)(i) adding a label to each of the $A_c$ continuous attribute lists, the discrete attribute list and the cost attribute list, such that the label is an index of a tuple to which the respective attribute belongs within the relational data table;
(c)(ii) adding a label to the cost list, such that the label is a cost flag that indicates whether the tuple containing the cost output value is enclosed within the hyper-rectangle, such that the cost flag is initially set to one.

18. The method of claim 17, wherein, step (f) further including steps of:
(f)(i) determining the discrete attribute value enclosed within the plurality of points along an edge of the hyper-rectangle with a lowest average cost output value using reduction;
(f)(ii) determining the continuous attribute value enclosed within the plurality of points along an edge of the hyper-rectangle with a lowest average cost output value using reduction;
(f)(iii) comparing the lowest average cost output value determined in step (f)(i) with the lowest average cost output value determined in step (f)(ii) to determine an attribute with the lowest average cost output value;
(f)(iv) removing all continuous attribute value points and all discrete attribute value points of the tuples containing the attribute determined in step (f)(iii) from the hyper-rectangle by setting the cost flag to zero using the index of the attribute to reference the cost flag in the cost list contained in each of the plurality of processors using the one to all broadcast; and
(f)(v) repeating steps (f)(i) to (f)(iv) until the count of the points within the hyper-rectangle equals $\beta_0$.

19. The method of claim 18, wherein a total cost output is a sum of the cost output values over the multidimensional space enclosed by the hyper-rectangle following step (f), and the cost attribute list includes a cost counter, step (g) further including steps of:
(g)(i) for each tuple with the cost flag set to zero, incrementing the cost counter for each point belonging to the tuple that is not enclosed with the hyper-rectangle among each of the plurality of portions of the shared disk;
(g)(ii) determining the discrete attribute value outside of the points enclosed by the hyper-rectangle with a highest average cost output value using reduction;
(g)(iii) determining the continuous attribute value outside of the points enclosed by the hyper-rectangle with a highest average cost output value using reduction;
(g)(iv) comparing the highest average cost output value determined in step (g)(ii) with the highest average cost output value determined in step (g)(iii) and determine which attribute with the highest average cost output value;
(g)(v) decrementing the cost counter for all continuous attribute value points and all discrete attribute value points belonging to the tuples containing the attribute determined in step (g)(iv) using the index of the attribute to reference the cost flag in the cost list contained in each of the plurality of processors using the one to all broadcast, such that attributes with the cost counter equal to zero are enclosed within the hyper-rectangle; and
(g)(vi) repeating steps (g)(i) to (g)(v) until a sum of the cost output value over the plurality of points enclosed by the hyper-rectangle is less than the total cost output.

\* \* \* \* \*